US011819365B2

United States Patent
Crawford et al.

(10) Patent No.: US 11,819,365 B2
(45) Date of Patent: *Nov. 21, 2023

(54) SYSTEM AND METHOD FOR MEASURING DEPTH OF INSTRUMENTATION

(71) Applicant: GLOBUS MEDICAL, INC., Audubon, PA (US)

(72) Inventors: Neil Crawford, Chandler, AZ (US); Chris Major, Reisterstown, MD (US)

(73) Assignee: Globus Medical, Inc., Audubon, PA (US)

( * ) Notice: Subject to any disclaimer, the term of this patent is extended or adjusted under 35 U.S.C. 154(b) by 714 days.

This patent is subject to a terminal disclaimer.

(21) Appl. No.: 16/824,746

(22) Filed: Mar. 20, 2020

(65) Prior Publication Data

US 2020/0229888 A1 Jul. 23, 2020

Related U.S. Application Data

(63) Continuation of application No. 15/343,255, filed on Nov. 4, 2016, now Pat. No. 10,624,710, which is a
(Continued)

(51) Int. Cl.
*A61B 90/00* (2016.01)
*A61B 34/30* (2016.01)
(Continued)

(52) U.S. Cl.
CPC .............. *A61B 90/06* (2016.02); *A61B 5/064* (2013.01); *A61B 17/3423* (2013.01);
(Continued)

(58) Field of Classification Search
CPC ..... A61B 90/06; A61B 5/064; A61B 17/3423; A61B 34/20; A61B 34/30; A61B 90/98;
(Continued)

(56) References Cited

U.S. PATENT DOCUMENTS

| 4,150,293 A | 4/1979 | Franke |
| 5,020,933 A | 6/1991 | Salvestro et al. |

(Continued)

FOREIGN PATENT DOCUMENTS

| AU | 2015234609 A1 | 10/2016 |
| CN | 1536975 A | 10/2004 |

(Continued)

OTHER PUBLICATIONS

US 8,231,638 B2, 07/2012, Swarup et al. (withdrawn)
(Continued)

*Primary Examiner* — Oommen Jacob

(57) ABSTRACT

Devices, systems, and methods for measuring the distance and/or depth to a target bone for surgery using a robotic surgical system. The surgical robot system may be configured to depict the distance from a guide tube of the robot to a target bone of a patient as a vector. The vector may represent a view of the guide tube when the guide tube's central axis is coincident with a line of intersection of two viewplanes of a 2D image of the target bone, for example, one viewplane being sagittal and one viewplane being axial.

15 Claims, 17 Drawing Sheets

Related U.S. Application Data continuation-in-part of application No. 15/157,444, filed on May 18, 2016, which is a continuation-in-part of application No. 15/095,883, filed on Apr. 11, 2016, now Pat. No. 10,893,912, which is a continuation-in-part of application No. 14/062,707, filed on Oct. 24, 2013, now Pat. No. 10,357,184, which is a continuation-in-part of application No. 13/924,505, filed on Jun. 21, 2013, now Pat. No. 9,782,229.

(60) Provisional application No. 61/800,527, filed on Mar. 15, 2013, provisional application No. 61/662,702, filed on Jun. 21, 2012.

(51) Int. Cl.

| | | |
|---|---|---|
| *A61B 17/34* | (2006.01) | |
| *A61B 34/20* | (2016.01) | |
| *A61B 90/98* | (2016.01) | |
| *A61B 5/06* | (2006.01) | |
| *A61B 90/96* | (2016.01) | |
| *A61B 90/11* | (2016.01) | |
| *A61B 17/00* | (2006.01) | |
| *A61B 17/17* | (2006.01) | |
| *A61B 34/00* | (2016.01) | |

(52) U.S. Cl.
CPC .............. *A61B 34/20* (2016.02); *A61B 34/30* (2016.02); *A61B 90/96* (2016.02); *A61B 90/98* (2016.02); *A61B 17/17* (2013.01); *A61B 34/25* (2016.02); *A61B 90/11* (2016.02); *A61B 2017/00876* (2013.01); *A61B 2034/2051* (2016.02); *A61B 2034/2055* (2016.02); *A61B 2034/2057* (2016.02); *A61B 2034/2059* (2016.02); *A61B 2034/2072* (2016.02); *A61B 2090/034* (2016.02); *A61B 2090/061* (2016.02); *A61B 2090/062* (2016.02); *A61B 2090/0811* (2016.02); *A61B 2090/373* (2016.02); *A61B 2090/376* (2016.02); *A61B 2090/3762* (2016.02); *A61B 2090/3937* (2016.02); *A61B 2090/3945* (2016.02)

(58) Field of Classification Search
CPC ............ A61B 90/11; A61B 2034/2072; A61B 2090/062
See application file for complete search history.

(56) References Cited

U.S. PATENT DOCUMENTS

| | | |
|---|---|---|
| 5,246,010 A | 9/1993 | Gazzara et al. |
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |

(56) References Cited

U.S. PATENT DOCUMENTS

| | | |
|---|---|---|
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,207,995 B1 | 4/2007 | Vandewalle |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Winash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 3,004,121 A1 | 8/2011 | Sartor |
| 7,988,215 B2 | 8/2011 | Seibold |
| 7,996,110 B2 | 8/2011 | Lipow et al. |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 3,046,057 A1 | 10/2011 | Clarke |
| 8,035,685 B2 | 10/2011 | Jensen |
| 8,046,054 B2 | 10/2011 | Kim et al. |
| 3,054,184 A1 | 11/2011 | Cline et al. |
| 3,054,752 A1 | 11/2011 | Druke et al. |
| 3,062,288 A1 | 11/2011 | Cooper et al. |
| 3,066,524 A1 | 11/2011 | Burbank et al. |
| 8,052,688 B2 | 11/2011 | Wolf, II |
| 8,057,397 B2 | 11/2011 | Li et al. |
| 8,057,407 B2 | 11/2011 | Martinelli et al. |
| 8,062,375 B2 | 11/2011 | Glerum et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |

(56) References Cited

U.S. PATENT DOCUMENTS

| | | |
|---|---|---|
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,313,430 B1 | 11/2012 | Pimenta |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Greer et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |

(56) References Cited

U.S. PATENT DOCUMENTS

| | | |
|---|---|---|
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,463,073 B2 | 10/2016 | Gill et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 10,575,906 B2 | 3/2020 | Wu |
| 2001/0036302 A1 | 11/2001 | Miller |
| 2002/0035321 A1 | 3/2002 | Bucholz et al. |
| 2003/0125622 A1 | 7/2003 | Schweikard et al. |
| 2003/0161442 A1 | 8/2003 | Zeiss |
| 2004/0019263 A1 | 1/2004 | Jutras et al. |
| 2004/0024311 A1 | 2/2004 | Quaid |
| 2004/0034302 A1 | 2/2004 | Abovitz et al. |
| 2004/0068172 A1 | 4/2004 | Nowinski et al. |
| 2004/0076259 A1 | 4/2004 | Jensen et al. |
| 2004/0097952 A1 | 5/2004 | Sarin et al. |
| 2004/0153191 A1 | 8/2004 | Grimm et al. |
| 2004/0157188 A1 | 8/2004 | Luth et al. |
| 2004/0215071 A1 | 10/2004 | Frank et al. |
| 2005/0085714 A1 | 4/2005 | Foley et al. |
| 2005/0096502 A1 | 5/2005 | Khalili |
| 2005/0107679 A1 | 5/2005 | Geiger et al. |
| 2005/0119639 A1 | 6/2005 | McCombs et al. |
| 2005/0143651 A1 | 6/2005 | Verard et al. |
| 2005/0149045 A1 | 7/2005 | Elliott |
| 2005/0165299 A1* | 7/2005 | Kressy ................ A61B 90/11 606/130 |
| 2005/0171558 A1 | 8/2005 | Abovitz et al. |
| 2005/0215888 A1 | 9/2005 | Grimm et al. |
| 2006/0036264 A1 | 2/2006 | Selover et al. |
| 2006/0100610 A1 | 5/2006 | Wallace et al. |
| 2006/0142657 A1 | 6/2006 | Quaid et al. |
| 2006/0173329 A1 | 8/2006 | Marquart et al. |
| 2006/0178559 A1 | 8/2006 | Kumar et al. |
| 2006/0184396 A1 | 8/2006 | Dennis et al. |
| 2006/0241416 A1 | 10/2006 | Marquart et al. |
| 2006/0264963 A1 | 11/2006 | Reed et al. |
| 2006/0291612 A1 | 12/2006 | Nishide et al. |
| 2007/0001879 A1 | 1/2007 | Kaftan et al. |
| 2007/0015987 A1 | 1/2007 | Benlloch Baviera et al. |
| 2007/0016009 A1 | 1/2007 | Lakin et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0078475 A1 | 4/2007 | Bodduluri et al. |
| 2007/0118140 A1* | 5/2007 | Baur ................ A61B 17/152 606/87 |
| 2007/0122020 A1 | 5/2007 | Claus et al. |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2007/0238985 A1 | 10/2007 | Smith et al. |
| 2008/0004523 A1 | 1/2008 | Jensen |
| 2008/0010706 A1 | 1/2008 | Moses et al. |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0119725 A1 | 5/2008 | Lloyd |
| 2008/0144906 A1 | 6/2008 | Allred et al. |
| 2008/0154389 A1 | 6/2008 | Smith et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0188934 A1 | 8/2008 | Moser et al. |
| 2008/0200794 A1 | 8/2008 | Techman et al. |
| 2008/0214922 A1 | 9/2008 | Hartmann et al. |
| 2008/0228068 A1 | 9/2008 | Viswanathan et al. |
| 2008/0228195 A1 | 9/2008 | von Jako et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0099445 A1 | 4/2009 | Burger |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0234217 A1* | 9/2009 | Mire ................ A61B 34/20 600/407 |
| 2009/0240141 A1 | 9/2009 | Neubauer et al. |
| 2009/0254326 A1 | 10/2009 | Isaacs |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2009/0306480 A1 | 12/2009 | Protopsaltis |
| 2009/0306499 A1 | 12/2009 | Van Vorhis et al. |
| 2010/0022874 A1 | 1/2010 | Wang et al. |
| 2010/0039506 A1 | 2/2010 | Sarvestani et al. |
| 2010/0046718 A1 | 2/2010 | Weiser et al. |
| 2010/0076305 A1 | 3/2010 | Maier-Hein et al. |
| 2010/0114288 A1 | 5/2010 | Haller et al. |
| 2010/0125286 A1 | 5/2010 | Wang et al. |
| 2010/0130986 A1 | 5/2010 | Mailloux et al. |
| 2010/0174410 A1 | 7/2010 | Greer et al. |
| 2010/0228117 A1 | 9/2010 | Hartmann |
| 2010/0228265 A1 | 9/2010 | Prisco |
| 2010/0228340 A1 | 9/2010 | Erbel et al. |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0019884 A1 | 1/2011 | Blau |
| 2011/0020084 A1 | 1/2011 | Brett et al. |
| 2011/0022229 A1 | 1/2011 | Jang et al. |

(56) References Cited

U.S. PATENT DOCUMENTS

| | | |
|---|---|---|
| 2011/0040305 A1 | 2/2011 | Gomez et al. |
| 2011/0071347 A1 | 3/2011 | Rogers et al. |
| 2011/0077504 A1 | 3/2011 | Fischer et al. |
| 2011/0082468 A1 | 4/2011 | Hagag et al. |
| 2011/0098553 A1 | 4/2011 | Robbins et al. |
| 2011/0137152 A1 | 6/2011 | Li |
| 2011/0184245 A1 | 7/2011 | Xia et al. |
| 2011/0190588 A1 | 8/2011 | McKay |
| 2011/0213379 A1 | 9/2011 | Blau et al. |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0257653 A1 | 10/2011 | Hughes et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306873 A1 | 12/2011 | Shenai et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0289820 A1 | 11/2012 | Rohling |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0051647 A1 | 2/2013 | Miao et al. |
| 2013/0060146 A1 | 3/2013 | Yang et al. |
| 2013/0060337 A1 | 3/2013 | Petersheim et al. |
| 2013/0064427 A1 | 3/2013 | Picard et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0165948 A1 | 6/2013 | Popovic |
| 2013/0172731 A1* | 7/2013 | Gole ............ A61B 6/506 600/424 |
| 2013/0178867 A1 | 7/2013 | Farritor et al. |
| 2013/0178868 A1 | 7/2013 | Roh |
| 2013/0178870 A1 | 7/2013 | Schena |
| 2013/0184873 A1 | 7/2013 | Namiki |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0268007 A1 | 10/2013 | Rezach et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0279784 A1 | 10/2013 | Gill |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345718 A1 | 12/2013 | Crawford et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0052150 A1 | 2/2014 | Taylor et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088410 A1 | 3/2014 | Wu |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135744 A1 | 5/2014 | Stein et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0200587 A1 | 7/2014 | Pompee et al. |
| 2014/0130810 A1 | 8/2014 | Azizian et al. |
| 2014/0221819 A1 | 8/2014 | Sarment |
| 2014/0221822 A1 | 8/2014 | Ehlers et al. |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275955 A1 | 9/2014 | Crawford et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276943 A1 | 9/2014 | Bowling et al. |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |

(56) References Cited

U.S. PATENT DOCUMENTS

| | | |
|---|---|---|
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316420 A1 | 10/2014 | Ballard et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0336669 A1 | 11/2014 | Park |
| 2014/0343416 A1 | 11/2014 | Panescu et al. |
| 2014/0357989 A1 | 12/2014 | Hendriks et al. |
| 2014/0364720 A1 | 12/2014 | Darrow et al. |
| 2014/0371577 A1 | 12/2014 | Maillet et al. |
| 2015/0032164 A1 | 1/2015 | Crawford et al. |
| 2015/0039034 A1 | 2/2015 | Frankel et al. |
| 2015/0049174 A1 | 2/2015 | Lee et al. |
| 2015/0085970 A1 | 3/2015 | Bouhnik et al. |
| 2015/0100066 A1* | 4/2015 | Kostrzewski .......... A61B 34/30 606/130 |
| 2015/0100067 A1 | 4/2015 | Cavanagh et al. |
| 2015/0146847 A1 | 5/2015 | Liu |
| 2015/0150524 A1 | 6/2015 | Yorkston et al. |
| 2015/0157416 A1 | 6/2015 | Andersson |
| 2015/0157468 A1 | 6/2015 | Wakayama et al. |
| 2015/0173810 A1 | 6/2015 | Biedermann et al. |
| 2015/0196261 A1 | 7/2015 | Funk |
| 2015/0196365 A1 | 7/2015 | Kostrzewski et al. |
| 2015/0209056 A1 | 7/2015 | Shoham et al. |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0030129 A1 | 2/2016 | Christian et al. |
| 2016/0063707 A1 | 3/2016 | Masumoto |
| 2016/0166329 A1 | 6/2016 | Langan et al. |
| 2016/0220320 A1 | 8/2016 | Crawford et al. |
| 2016/0235480 A1 | 8/2016 | Scholl et al. |
| 2016/0235492 A1 | 8/2016 | Morard et al. |
| 2016/0235493 A1 | 8/2016 | Leboeuf, II et al. |
| 2016/0249990 A1 | 9/2016 | Glozman et al. |
| 2016/0256225 A1 | 9/2016 | Crawford et al. |
| 2016/0296266 A1 | 10/2016 | Chandanson et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0000562 A1 | 1/2017 | Frank et al. |
| 2017/0007327 A1 | 1/2017 | Haider et al. |
| 2017/0020609 A1 | 1/2017 | Wentorf et al. |
| 2017/0079727 A1 | 3/2017 | Crawford et al. |
| 2017/0112552 A1 | 4/2017 | Sinnott et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0189126 A1 | 7/2017 | Weir |
| 2017/0202629 A1 | 7/2017 | Maillet et al. |
| 2017/0209222 A1 | 7/2017 | Gassner et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0245946 A1 | 8/2017 | Tabandeh et al. |
| 2017/0245951 A1 | 8/2017 | Crawford et al. |
| 2017/0258426 A1 | 9/2017 | Risher-Kelly et al. |
| 2017/0258535 A1 | 9/2017 | Crawford et al. |
| 2017/0265952 A1 | 9/2017 | Donhowe et al. |
| 2017/0273748 A1 | 9/2017 | Hourtash et al. |
| 2017/0296277 A1 | 10/2017 | Hourtash et al. |
| 2017/0333137 A1 | 11/2017 | Roessler |
| 2017/0360493 A1 | 12/2017 | Zucher et al. |
| 2018/0008355 A1 | 1/2018 | Mozes et al. |
| 2018/0028108 A1* | 2/2018 | Shluzas ................ A61B 5/0077 |
| 2018/0042464 A1 | 2/2018 | Arai et al. |
| 2018/0049825 A1 | 2/2018 | Kwon et al. |
| 2018/0064496 A1 | 3/2018 | Hladio et al. |
| 2018/0064497 A1 | 3/2018 | Hussain et al. |
| 2018/0066794 A1 | 3/2018 | Okuda et al. |
| 2018/0092699 A1 | 4/2018 | Finley |
| 2018/0200016 A1 | 7/2018 | Chappuis |
| 2018/0249981 A1 | 9/2018 | Johnson et al. |
| 2018/0325608 A1 | 11/2018 | Kang et al. |
| 2018/0325610 A1 | 11/2018 | Cameron et al. |

FOREIGN PATENT DOCUMENTS

| | | |
|---|---|---|
| CN | 1714742 A | 1/2006 |
| CN | 102036615 A | 4/2011 |
| CN | 202027725 U | 11/2011 |
| CN | 102438551 A | 5/2012 |
| CN | 102596062 A | 7/2012 |
| CN | 102612350 A | 7/2012 |
| CN | 102933163 A | 2/2013 |
| CN | 103945764 A | 7/2014 |
| CN | 104334110 A | 2/2015 |
| CN | 104994805 A | 10/2015 |
| CN | 105101903 A | 11/2015 |
| CN | 105939687 A | 9/2016 |
| CN | 106163446 A | 11/2016 |
| CN | 106691600 A | 5/2017 |
| CN | 106999168 A | 8/2017 |
| CN | 106999245 A | 8/2017 |
| CN | 107088091 A | 8/2017 |
| CN | 107405170 A | 11/2017 |
| CN | 107545585 A | 1/2018 |
| CN | 108601569 A | 9/2018 |
| CN | 108652743 B | 10/2018 |
| CN | 209153975 U | 7/2019 |
| CN | 107847275 B | 10/2020 |
| DE | 102014221469 A1 | 4/2016 |
| DE | 102012215001 B4 | 12/2021 |
| EP | 1103223 A2 | 5/2001 |
| EP | 1224918 A2 | 7/2002 |
| EP | 1346687 A1 | 9/2003 |
| EP | 1523950 A1 | 4/2005 |
| EP | 2468207 A1 | 6/2012 |
| EP | 2471617 A1 | 7/2012 |
| EP | 3181085 A1 | 6/2017 |
| EP | 3391848 A2 | 10/2018 |
| EP | 3517069 A1 | 7/2019 |
| JP | 3-118053 A | 5/1991 |
| JP | 11-313837 A | 11/1999 |
| JP | 2001135734 A | 5/2001 |
| JP | 2002253574 A | 9/2002 |
| JP | 2004518475 A | 6/2004 |
| JP | 2005-533579 A | 11/2005 |
| JP | 2007-044488 A | 2/2007 |
| JP | 2007-531543 A | 11/2007 |
| JP | 2007534351 A | 11/2007 |
| JP | 2007537835 A | 12/2007 |
| JP | 2008-507361 A | 3/2008 |
| JP | 2008507361 A | 3/2008 |
| JP | 2008188417 A | 8/2008 |
| JP | 2008-538184 A | 10/2008 |
| JP | 2009537229 A | 10/2009 |
| JP | 2011-120782 A | 6/2011 |
| JP | 2011-517594 A | 6/2011 |
| JP | 2012075507 A | 4/2012 |
| JP | 2013075195 A | 4/2013 |
| JP | 2013-541365 A | 11/2013 |
| JP | 2014036700 A | 2/2014 |
| JP | 2014097220 A | 5/2014 |
| JP | 2015-504721 A | 2/2015 |
| JP | 201536161 A | 2/2015 |
| JP | 2015100677 A | 6/2015 |
| JP | 2015119968 A | 7/2015 |
| JP | 2015521084 A | 7/2015 |
| JP | 2015528713 A | 10/2015 |
| JP | 2015-534480 A | 12/2015 |
| JP | 2015534845 A | 12/2015 |
| JP | 2016043211 A | 4/2016 |
| JP | 2016185225 A | 10/2016 |
| JP | 2016-193222 A | 11/2016 |
| JP | 2016193222 A | 11/2016 |

(56) References Cited

FOREIGN PATENT DOCUMENTS

| | | |
|---|---|---|
| JP | 2016539681 A | 12/2016 |
| JP | 2017087313 A | 5/2017 |
| JP | 2017176848 A | 10/2017 |
| JP | 2017530842 A | 10/2017 |
| JP | 2017221660 A | 12/2017 |
| JP | 2017223657 A | 12/2017 |
| JP | 2018011938 A | 1/2018 |
| JP | 2018-027288 A | 2/2018 |
| JP | 2018516107 A | 6/2018 |
| JP | 2018-114283 A | 7/2018 |
| JP | 2018523516 A | 8/2018 |
| JP | 2018-202156 A | 12/2018 |
| JP | 2021025802 A | 2/2021 |
| WO | 2005039417 A1 | 5/2005 |
| WO | 2009092164 A1 | 7/2009 |
| WO | 2009126953 A2 | 10/2009 |
| WO | 2011128766 A2 | 10/2011 |
| WO | 2012050634 A1 | 4/2012 |
| WO | 2013114823 A1 | 8/2013 |
| WO | 2013118047 A1 | 8/2013 |
| WO | 2013192598 A1 | 12/2013 |
| WO | 2014010760 A1 | 1/2014 |
| WO | 2014062890 A1 | 4/2014 |
| WO | 2014139023 A1 | 9/2014 |
| WO | 2015023665 A1 | 2/2015 |
| WO | 2015052718 A1 | 4/2015 |
| WO | 2015061638 A1 | 4/2015 |
| WO | 2015079775 A1 | 6/2015 |
| WO | 2015142762 A1 | 9/2015 |
| WO | 201613049 A1 | 1/2016 |
| WO | 2016087539 A2 | 6/2016 |
| WO | 2016114834 A2 | 7/2016 |
| WO | 2016152255 A1 | 9/2016 |
| WO | 2016154557 A1 | 9/2016 |
| WO | 2016170372 A1 | 10/2016 |
| WO | 2017221257 A1 | 2/2017 |
| WO | 2017127202 A1 | 7/2017 |
| WO | 2017147596 A1 | 8/2017 |
| WO | 2017186799 A1 | 11/2017 |
| WO | 2017204832 A1 | 11/2017 |
| WO | 2017221257 A1 | 12/2017 |
| WO | 2018075784 A1 | 4/2018 |
| WO | 2018165767 A1 | 9/2018 |
| WO | 2018183461 A1 | 10/2018 |
| WO | 2019193775 A1 | 10/2019 |

OTHER PUBLICATIONS

Andreas Aik et al: "Smart Device Assisted Method for Rod Length and Rod Radius Measurement in Percutaneous Pedicle Screw Surgery", Przeglad Elektrotechniczny, vol. 3, Mar. 5, 2016 (Mar. 5, 2016), pp. 30-33, XP055668769, PO ISSN: 0033-2097, DOI: 10.15199/48.2016.03.07.

Markelj et al.: "A review of 3D/2D registration methods for image-guided interventions", Medical Image Analysis, Oxford University Press, Oxford, GB, vol. 16, No. 3, pp. 642-661, Apr. 1, 2012.

Gong Ren Hui et al.: "Interactive initialization of 2D/3D rigid registration", Medical Physics, AIP, Melville, NY, US, vol. 40, No. 12, 14 pages, Dec. 2013.

Dumenil A et al.: "A versatile intensity-based 3D/2D rigid registration compatible with mobile C-arm for endovascular treatment of abdominal aortic aneurysm", International Journal of Computer Assisted Radiology and Surgery, Springer, DE, vol. 11, No. 9, pp. 1713-1729, May 26, 2016.

Marintschev et al.: "Navigation of vertebro-pelvic fixations based on CT-fluoro macthing", European Spine Journal, Springer, Berlin, DE, vol. 19, No. 11, pp. 1921-1927, Jun. 16, 2010.

Alk et al., "Smart Device Assisted Method for Rod Length and Rod Radius Measurement in Percutaneious Pedicle Screw Surgery", Prizeglad Elektrotechniczny, vol. 3, Mar. 5, 2016, pp. 30-33.

* cited by examiner

SYSTEM AND METHOD FOR MEASURING DEPTH OF INSTRUMENTATION

CROSS-REFERENCE TO RELATED APPLICATIONS

This application is a continuation of U.S. patent application Ser. No. 15/343,255, filed Nov. 4, 2016, which is a continuation-in-part of U.S. patent application Ser. No. 15/157,444 filed May 18, 2016, which is a continuation-in-part application of U.S. patent application Ser. No. 15/095,883 filed on Apr. 11, 2016 (published as U.S. Patent Publication No. 2016/0220320 A1), which is a continuation-in-part application of U.S. patent application Ser. No. 14/062,707 filed on Oct. 24, 2013 (published as U.S. Patent Publication No. 2014/0275955 A1), which is a continuation-in-part application of U.S. patent application Ser. No. 13/924,505 filed on Jun. 21, 2013 (published as U.S. Patent Publication No. 2013/0345718 A1, with corrected publication as U.S. Patent Publication No. 2016/0242849 A9), which is a nonprovisional patent application that claims priority to U.S. provisional patent application No. 61/662,702 filed on Jun. 21, 2012, and claims priority to U.S. provisional patent application No. 61/800,527 filed on Mar. 15, 2013, the entire contents of all of which are incorporated herein by reference.

FIELD OF THE INVENTION

The present disclosure relates to position recognition systems, and in particular, position recognition systems that allow measurement of instrumentation and tools in a patient using robot-assisted surgical techniques.

BACKGROUND OF THE INVENTION

Various medical procedures require the accurate localization of a three-dimensional position of a surgical instrument within the body in order to effect optimized treatment. For example, some surgical procedures to fuse vertebrae require that a surgeon drill multiple holes into the bone structure at specific locations. To achieve high levels of mechanical integrity in the fusing system, and to balance the forces created in the bone structure, it is necessary that the holes are drilled at the correct location. Vertebrae, like most bone structures, have complex shapes including non-planar curved surfaces making accurate and perpendicular drilling difficult. Conventionally, a surgeon manually holds and positions a drill guide tube by using a guidance system to overlay the drill tube's position onto a three dimensional image of the bone structure. This manual process is both tedious and time consuming. The success of the surgery is largely dependent upon the dexterity of the surgeon who performs it.

When a surgeon performs minimally invasive surgery and prepares to place a screw into bone, it is often desirable to insert a dilator tube from the surface of the skin through muscle and connective tissue down to a position where the distal end of the dilator tube is adjacent to bone. The dilator tube serves as a corridor through which drilling and other surgical steps can occur. Currently, the most frequently used method for gauging whether the dilator is sufficiently far enough inserted is to record x-ray images, which is effective but exposes the patient and surgical staff to x-rays and can be time consuming. If image guidance were to be used instead of x-rays, it would spare the patient and staff some exposure to x-rays. However, a tracking array mounted on a dilator tube has the drawbacks that it is unwieldy and obtrusive to the surgeon in an area where a great deal of surgical activity is occurring.

Thus, there is a need to be able to measure the depth of surgical instrumentation in a manner that limits the exposure of the patient and medical staff to unnecessary radiation from imaging systems without obstructing and impeding a medical staff's ability to perform the surgical operation on the patient. The present disclosure overcomes the disadvantages of current traditional surgical techniques and robot-assisted surgical techniques. For example, using known positions of components of a robot surgical system allows a surgeon to position a long shaft such as a dilator tube within a secondary tracked tube, such as the robot's end effector guide tube or a free tracked external guide tube, to a depth such that the dilator tube contacts the target bony structure. This positioning would allow tracking the dilator tube indirectly without tracking the dilator itself and without the use of x-ray images as it is further inserted into a patient.

SUMMARY OF THE INVENTION

To meet this and other needs, devices, systems, and methods for determining the distance or depth for a surgical instrument to contact a target bone of a patient during robot assisted surgery is provided.

According to one exemplary embodiment, a surgical robot system may be configured to determine a distance for a surgical instrument to contact a target bone of a patient during a surgical operation. The system may include a guide tube comprising a tracking marker and wherein the guide tube may be configured to receive the surgical instrument, a tracking subsystem having a position sensor that recognizes the tracking marker in a navigational space, a platform interface module that may be configured to receive a signal from the tracking subsystem indicative of a position of the guide tube based on the tracking marker, and a computer subsystem, including a computer and a display, that may be configured to receive a first viewplane scan of the target bone and a second viewplane scan of the target bone. The first viewplane and the second viewplane may form an intersection of views of the target bone. The computer subsystem may also be configured to receive the position of the guide tube from the platform interface module and may depict a vector indicative of the distance to contact the target bone of the patient, relative to a distal portion of the guide tube, on at least one of the first viewplane scan and the second viewplane scan, and wherein the vector may represent a central axis of the guide tube being coincident to the intersection.

According to another embodiment, a method for determining the distance for a surgical instrument to contact a target bone of a patient during a surgical operating using a robotic surgical system may be provided. The method may include receiving, by a computer subsystem having a computer and a display, a first viewplane scan of the target bone and a second viewplane scan of the target bone, wherein the first viewplane and the second viewplane form an intersection of views of the target bone in an image space. The method may also include receiving, by the computer subsystem, a position of a guide tube in navigational space, and determining, by the computer, a distance between a distal portion of the guide tube to the target bone of the patient, wherein the distance may be determined such that a central axis of the guide tube is coincident to the intersection. The method may also include depicting, via the display, a vector indicative of the distance to contact the target bone of the patient on at least one of the first viewplane scan and the second viewplane scan.

BRIEF DESCRIPTION OF THE DRAWINGS

The invention and the following detailed description of certain embodiments thereof may be understood by reference to the following figures.

DETAILED DESCRIPTION OF THE INVENTION

Figure 1:
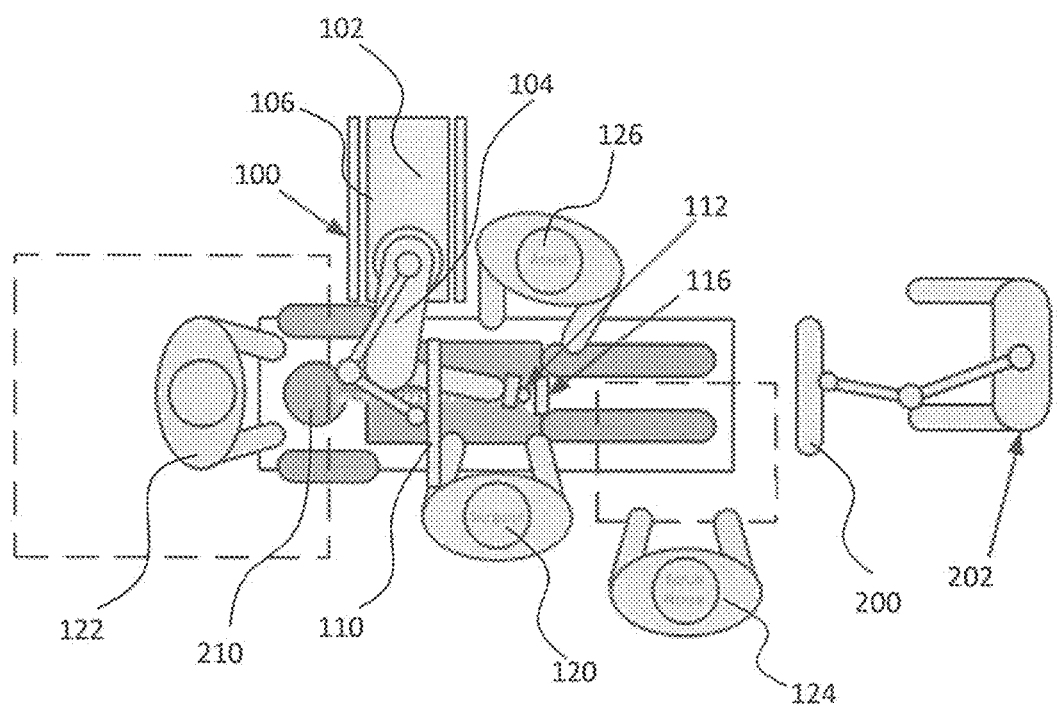
FIG. 1 is an overhead view of a potential arrangement for locations of the robotic system, patient, surgeon, and other medical personnel during a surgical procedure.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
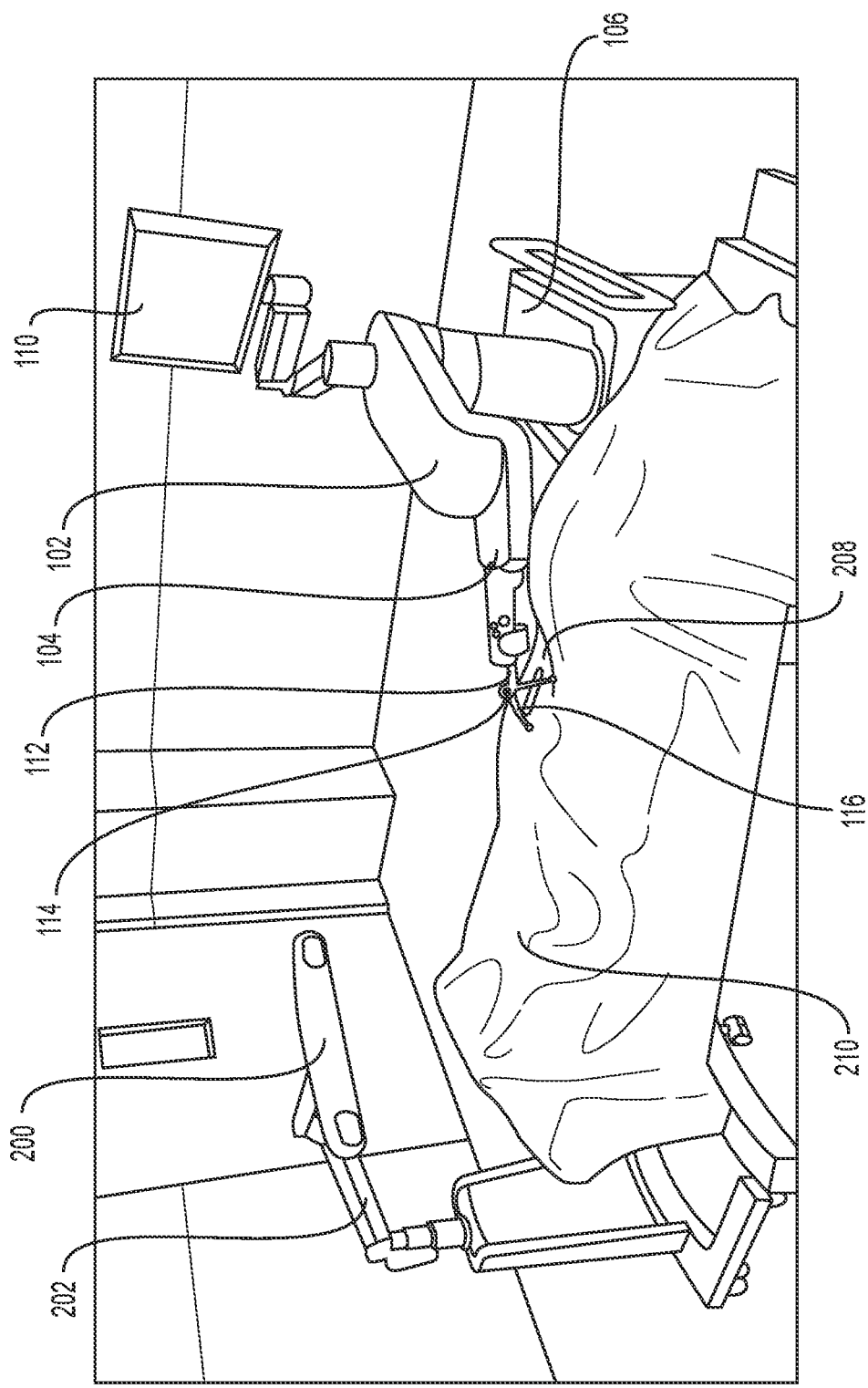
FIG. 2 illustrates the robotic system including positioning of the surgical robot and the camera relative to the patient according to one embodiment.

Turning now to the drawing, FIGS. 1 and 2 illustrate a surgical robot system 100 in accordance with an exemplary embodiment. Surgical robot system 100 may include, for example, a surgical robot 102, one or more robot arms 104, a base 106, a display 110, an end effector 112, for example, including a guide tube 114, and one or more tracking markers 118. The surgical robot system 100 may include a patient tracking device 116 also including one or more tracking markers 118, which is adapted to be secured directly to the patient 210 (e.g., to the bone of the patient 210). The surgical robot system 100 may also utilize a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 in a given measurement volume viewable from the perspective of the camera 200. The camera 200 may scan the given measurement volume and detect the light that comes from the markers 118 in order to identify and determine the position of the markers 118 in three dimensions. For example, active markers 118 may include infrared-emitting markers that are activated by an electrical signal (e.g., infrared light emitting diodes (LEDs)), and passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end effector 112 and the display 110. A surgical assistant 126 may be positioned across from the surgeon 120 again with access to both the end effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End effector 112 may be coupled to the robot arm 104 and controlled by at least one motor. In exemplary embodiments, end effector 112 can comprise a guide tube 114, which is able to receive and orient a surgical instrument 608 (described further herein) used to perform surgery on the patient 210. As used herein, the term "end effector" is used interchangeably with the terms "end-effectuator" and "effectuator element." Although generally shown with a guide tube 114, it will be appreciated that the end effector 112 may be replaced with any suitable instrumentation suitable for use in surgery. In some embodiments, end effector 112 can comprise any known structure for effecting the movement of the surgical instrument 608 in a desired manner.

The surgical robot 102 is able to control the translation and orientation of the end effector 112. The robot 102 is able to move end effector 112 along x-, y-, and z-axes, for example. The end effector 112 can be configured for selective rotation about one or more of the x-, y-, and z-axis, and a Z Frame axis (such that one or more of the Euler Angles (e.g., roll, pitch, and/or yaw) associated with end effector 112 can be selectively controlled). In some exemplary embodiments, selective control of the translation and orientation of end effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end effector 112 and/or the surgical instrument 608. Thus, in use, in exemplary embodiments, a physician or other user can operate the system 100, and has the option to stop, modify, or manually control the autonomous movement of end effector 112 and/or the surgical instrument 608. Further details of surgical robot system 100 including the control and movement of a surgical instrument 608 by surgical robot 102 can be found in co-pending U.S. patent application Ser. No. 13/924,505, which is incorporated herein by reference in its entirety.

The robotic surgical system 100 can comprise one or more tracking markers 118 configured to track the movement of robot arm 104, end effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, or on the end effector 112. In exemplary embodiments, at least one tracking marker 118 of the plurality of tracking markers 118 can be mounted or otherwise secured to the end effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screw driver, dilator, implant inserter, or the like). Thus, the tracking markers 118 enable each of the marked objects (e.g., the end effector 112, the patient 210, and the surgical tools 608) to be tracked by the robot 102. In exemplary embodiments, system 100 can use tracking information collected from each of the marked objects to calculate the orientation and location, for example, of the end effector 112, the surgical instrument 608 (e.g., positioned in the tube 114 of the end effector 112), and the relative position of the patient 210.

In exemplary embodiments, one or more of markers 118 may be optical markers. In some embodiments, the positioning of one or more tracking markers 118 on end effector 112 can maximize the accuracy of the positional measurements by serving to check or verify the position of end effector 112. Further details of surgical robot system 100 including the control, movement and tracking of surgical robot 102 and of a surgical instrument 608 can be found in co-pending U.S. patent application Ser. No. 13/924,505, which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
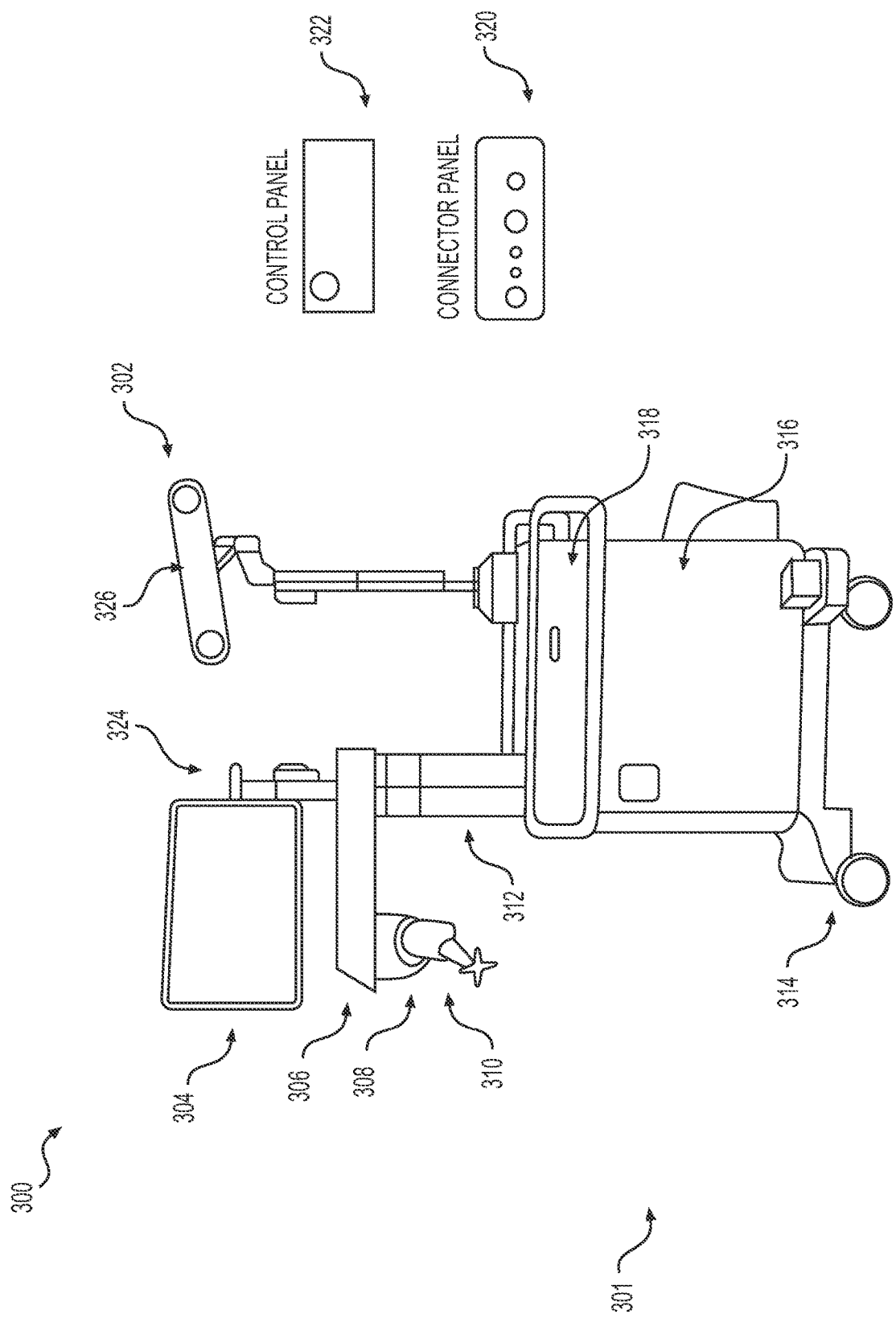
FIG. 3 illustrates a surgical robotic system in accordance with an exemplary embodiment.
Figure 4:
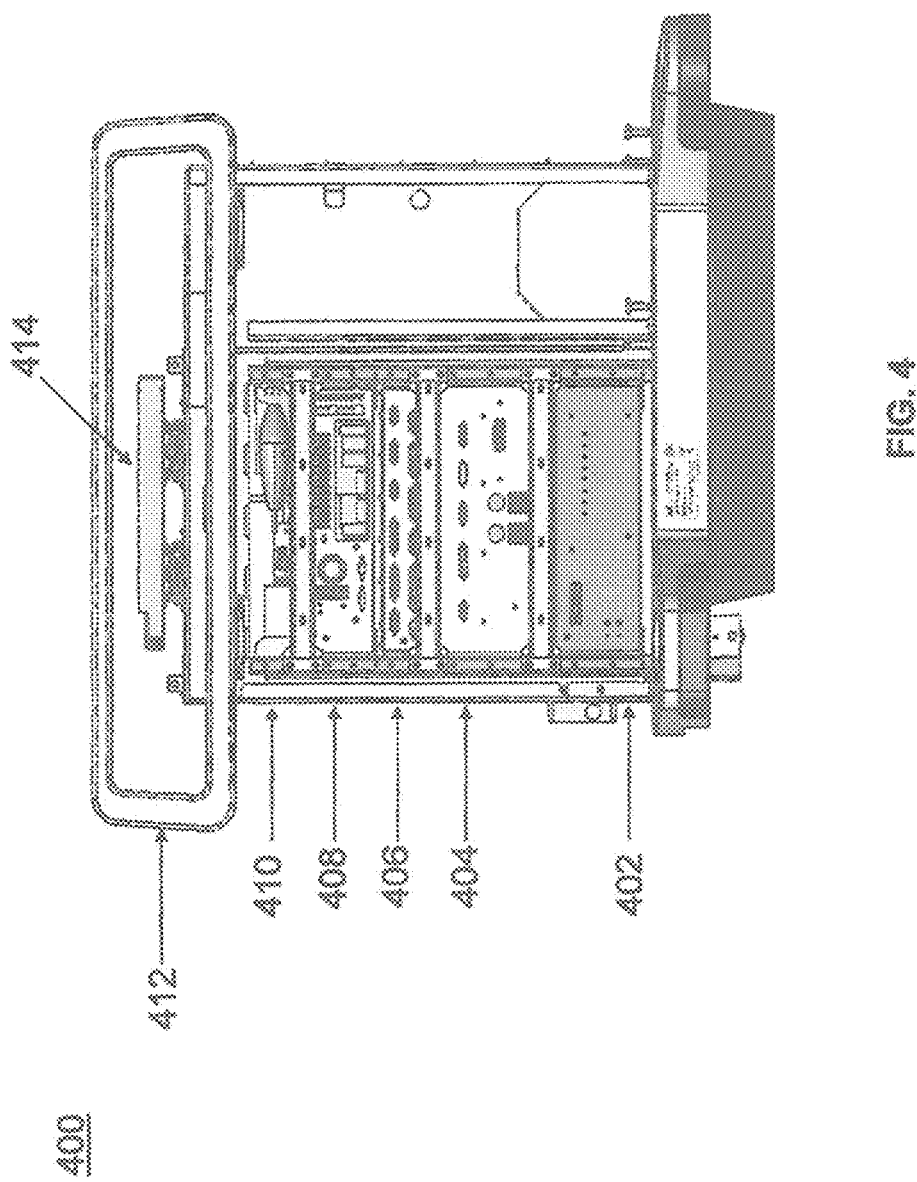
FIG. 4 illustrates a portion of a surgical robot in accordance with an exemplary embodiment.

Similar to surgical robot system 100, FIG. 3 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end effector 310, vertical column 312, casters 314, cabinet 316, tablet drawer 318, connector panel 320, control panel 322, and ring of information 324. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 1 and 2. FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
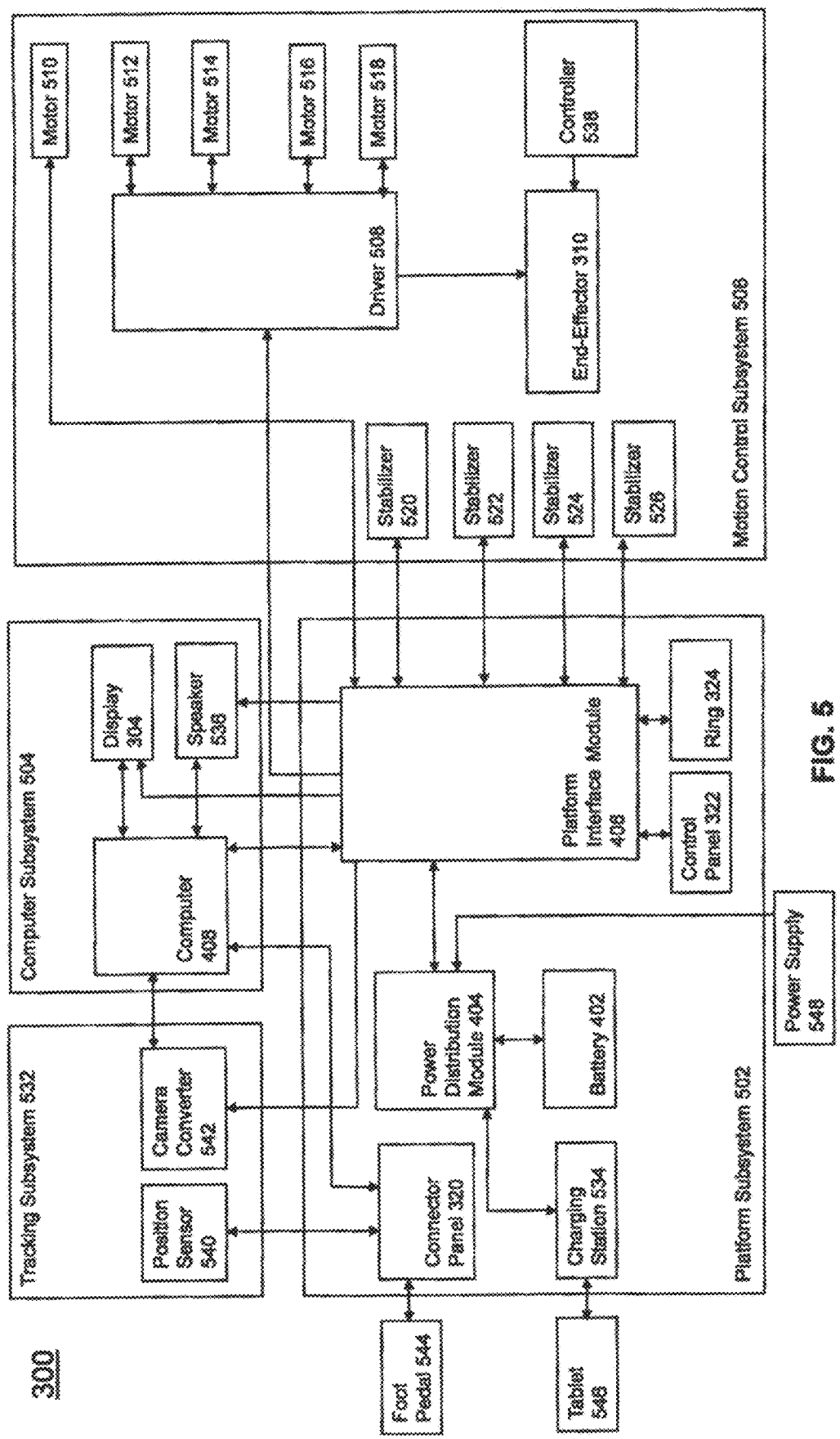
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein. Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure. Motion control subsystem 506 may be configured to physically move vertical column 312, upper arm 306, lower arm 308, or rotate end effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end effector 310 in a manner such that one may control the roll and one may control the tilt, thereby providing multiple angles that end effector 310 may be moved. These movements may be achieved by controller 538 which may control these movements through load cells disposed on end effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on three dimensional image of the patient's anatomy on display 304. The user may initiate this automatic movement by stepping on foot pedal 544 or some other input means.

Figure 6:
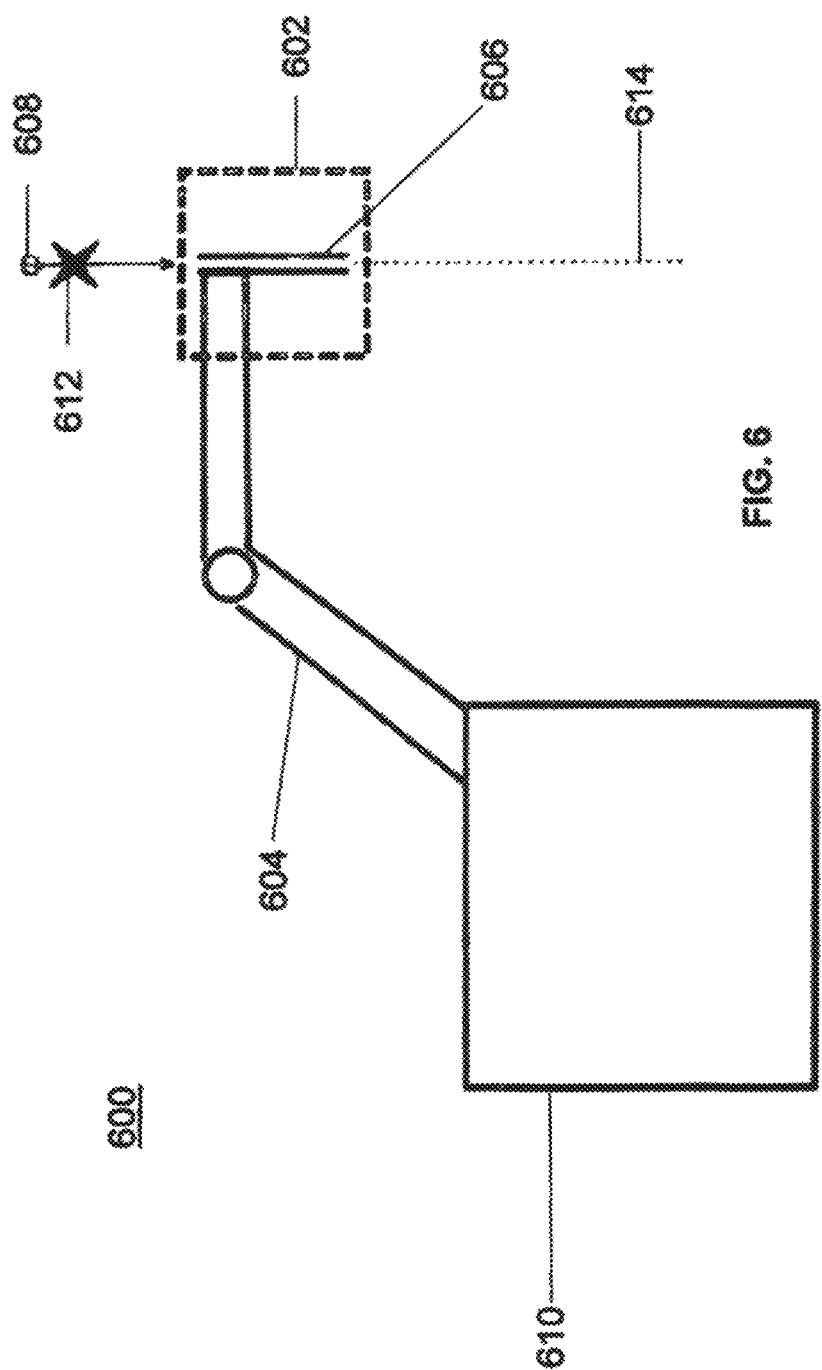
FIG. 6 illustrates a surgical robot in accordance with an exemplary embodiment.

FIG. 6 illustrates a surgical robot system 600 consistent with an exemplary embodiment. Surgical robot system 600 may comprise end effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end effector 602 so that surgical robot system 600 may assist a user (for example, a surgeon) in operating on the patient 210. Surgical robot system 600 may be consistent with previously described surgical robot system 100 and 300.

Figure 8:
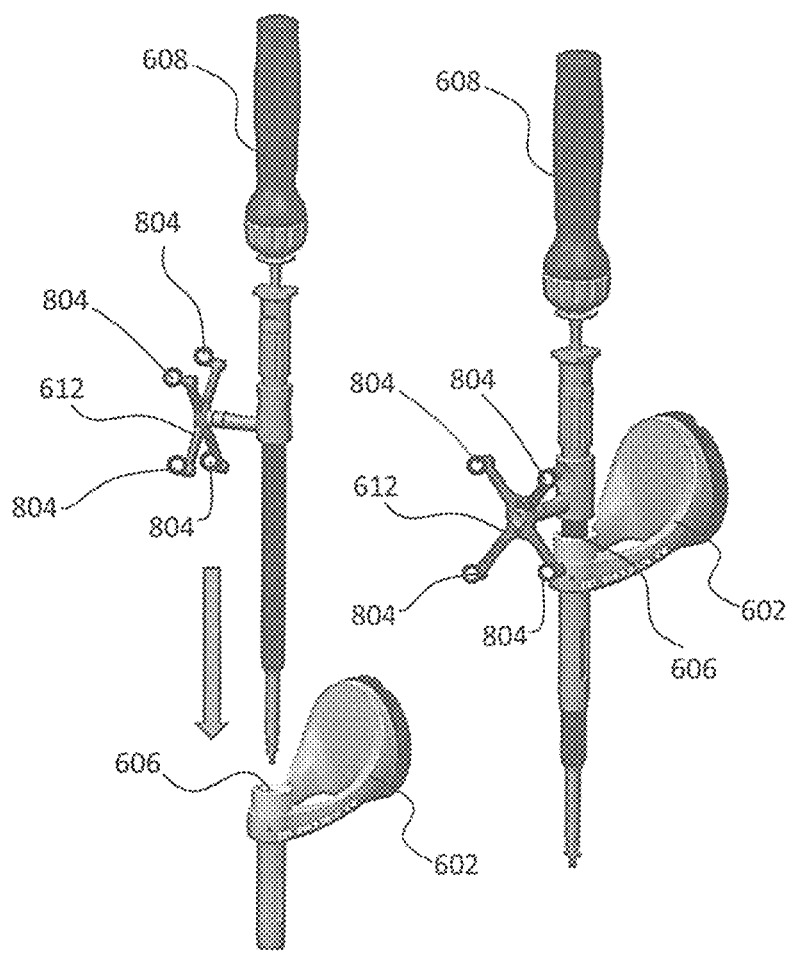
FIG. 8 illustrates a surgical instrument and the end effector, before and after, inserting the surgical instrument into the guide tube of the end effector according to one embodiment.

A tracking array 612 may be mounted on instrument 608 to monitor the location and orientation of instrument tool 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end effector 602, and/or the patient 210. The tracking devices may be consistent with those structures described in connection with camera stand 302 and tracking subsystem 532.

Figure 7:
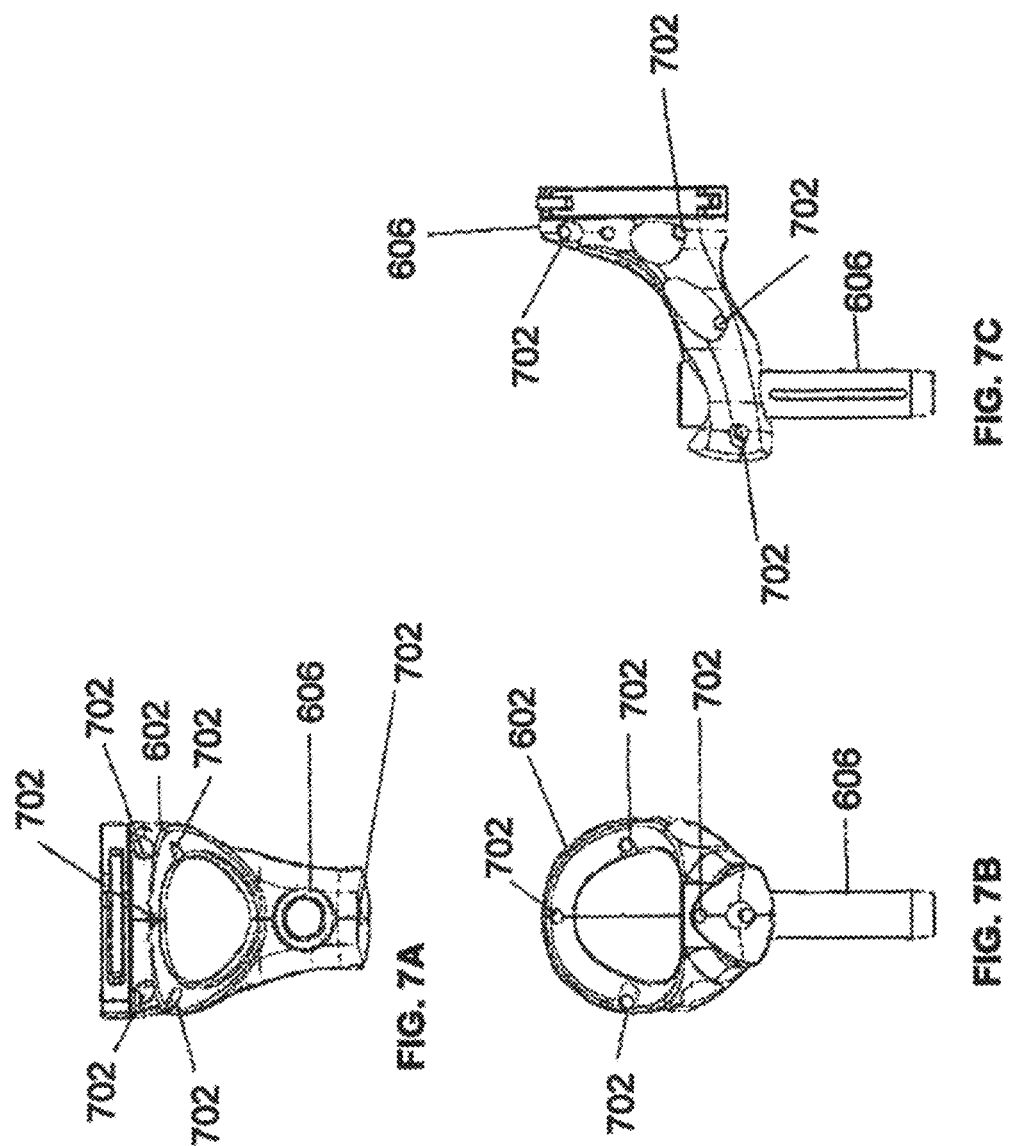
FIGS. 7A-7C illustrate an end effector in accordance with an exemplary embodiment.

FIGS. 7A, 7B, and 7C illustrate a top view, front view, and side view, respectively, of end effector 602 consistent with an exemplary embodiment. End effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end effector 602 may be controlled by the system 100, 300, 600, and when the markers 702 are deactivated, the end effector 602 may be locked in position and unable to be moved by the system 100, 300, 600.

Markers 702 may be disposed on or within end effector 602 in a manner such that the markers 702 are visible by one or more cameras 200, 326 or other tracking devices associated with the surgical robot system 100, 300, 600. The camera 200, 326 or other tracking devices may track end effector 602 as it moves to different positions and viewing angles by following the movement of tracking markers 702. The location of markers 702 and/or end effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end effector 602 is in a desirable position in relation to robot arm 604, robot base 610, the patient 210, and/or the user.

For example, as shown in FIG. 7A, markers 702 may be placed around the surface of end effector 602 so that a tracking device placed away from the surgical field 208 and facing toward the robot 102, 301 and the camera 200, 326 is able to view at least 3 of the markers 702 through a range of common orientations of the end effector 602 relative to the tracking device 100, 300, 600. For example, distribution of markers 702 in this way allows end effector 602 to be monitored by the tracking devices when end effector 602 is translated and rotated in the surgical field 208.

In addition, in exemplary embodiments, end effector 602 may be equipped with infrared (IR) receivers that can detect when an external camera 200, 326 is getting ready to read markers 702. Upon this detection, end effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end effector 602 and adjust the instrument 608 is evident in FIG. 8. The hollow tube or guide tube 114, 606 of the end effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screw driver is exemplified as the surgical tool 608, it will be appreciated that any suitable surgical tool 608 may be positioned by the end effector 602. By way of example, the surgical instrument 608 may include one or more of a guide wire, cannula, a retractor, a drill, a reamer, a screw driver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

Figure 9:
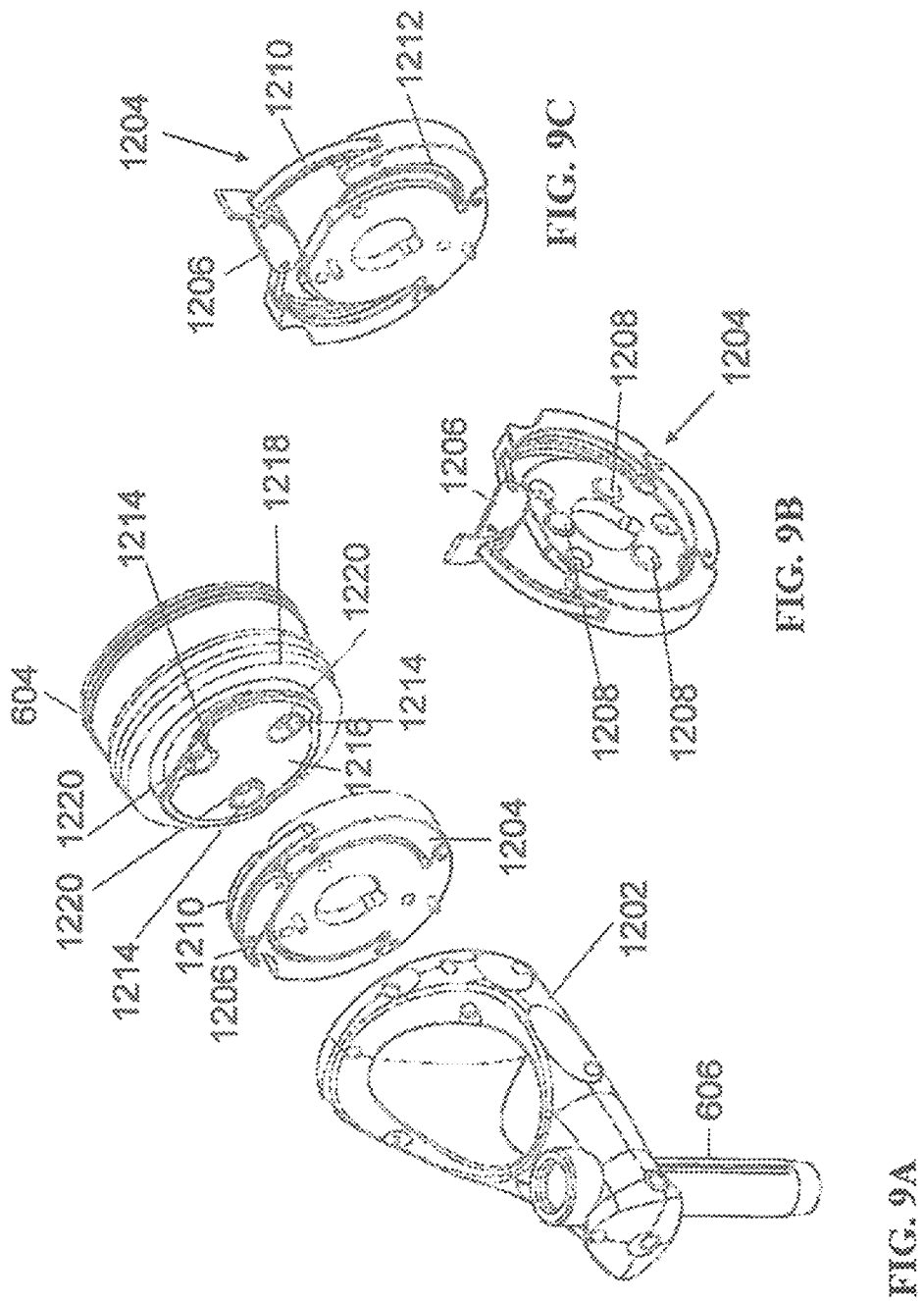
FIGS. 9A-9C illustrate portions of an end effector and robot arm in accordance with an exemplary embodiment.

FIGS. 9A-9C illustrate end effector 602 and a portion of robot arm 604 consistent with an exemplary embodiment. End effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220.

End effector 602 may mechanically interface and/or engage with the surgical robot system and robot arm 604 through one or more couplings. For example, end effector 602 may engage with robot arm 604 through a locating coupling and/or a reinforcing coupling. Through these couplings, end effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end effector 602 regardless of the orientation of end effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end effector 602 to robot arm 604 as lip 1212 and lip 1218 engage clamp 1204 in a manner to secure end effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end effector 602 may be robustly secured to robot arm 604.

Spring 1210 may be a curved beam in tension. Spring 1210 may be comprised of a material that exhibits high stiffness and high yield strain such as virgin PEEK (polyether-ether-ketone). The linkage between end effector 602 and robot arm 604 may provide for a sterile barrier between end effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end effector 602 and/or robot arm 604 that slips over an interface between end effector 602 and robot arm 604 and tightens with a screw mechanism, an over center linkage, or a cam mechanism.

Figure 10:
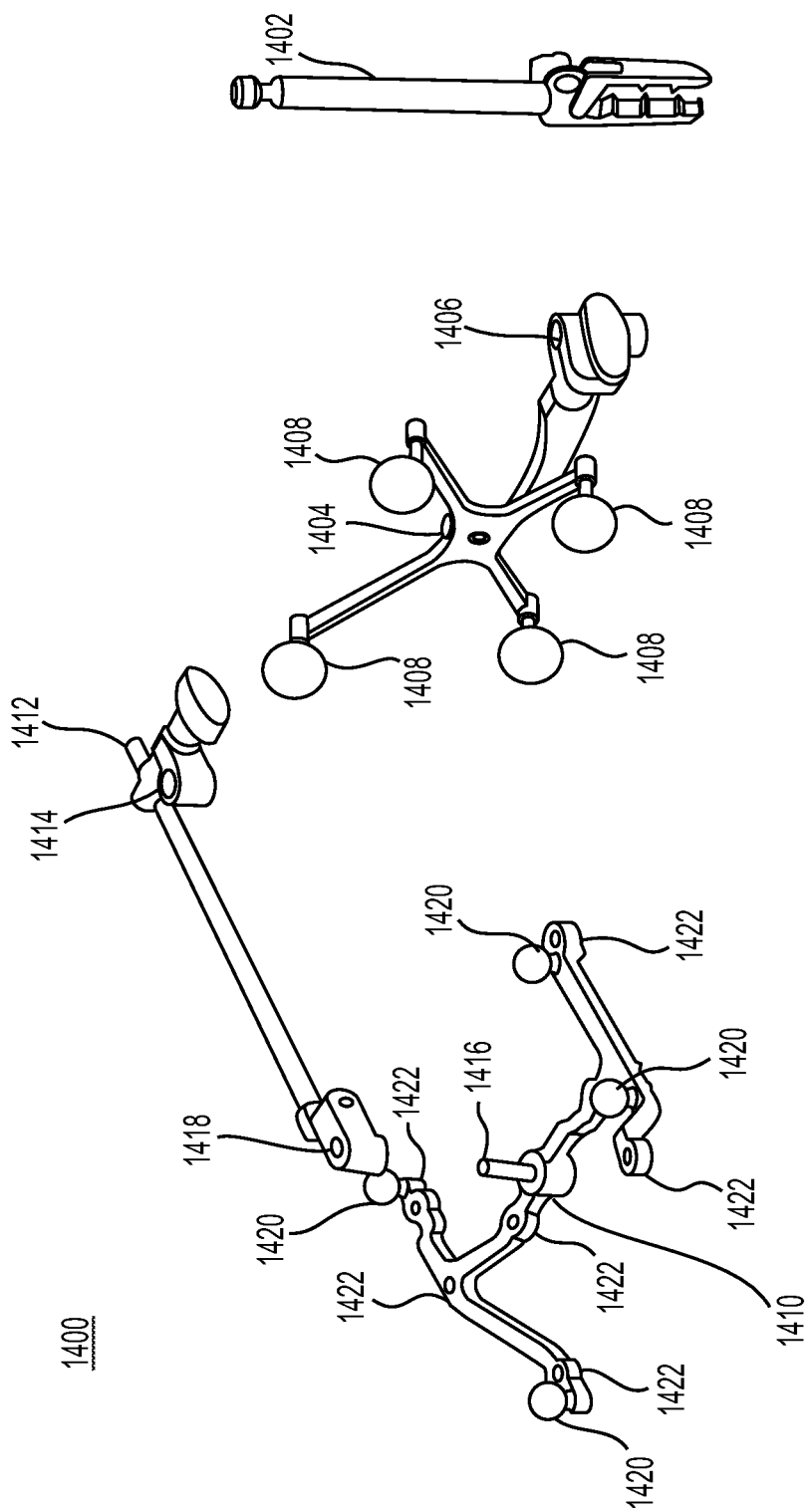
FIG. 10 illustrates a dynamic reference array, an imaging array, and other components in accordance with an exemplary embodiment.
Figure 11:
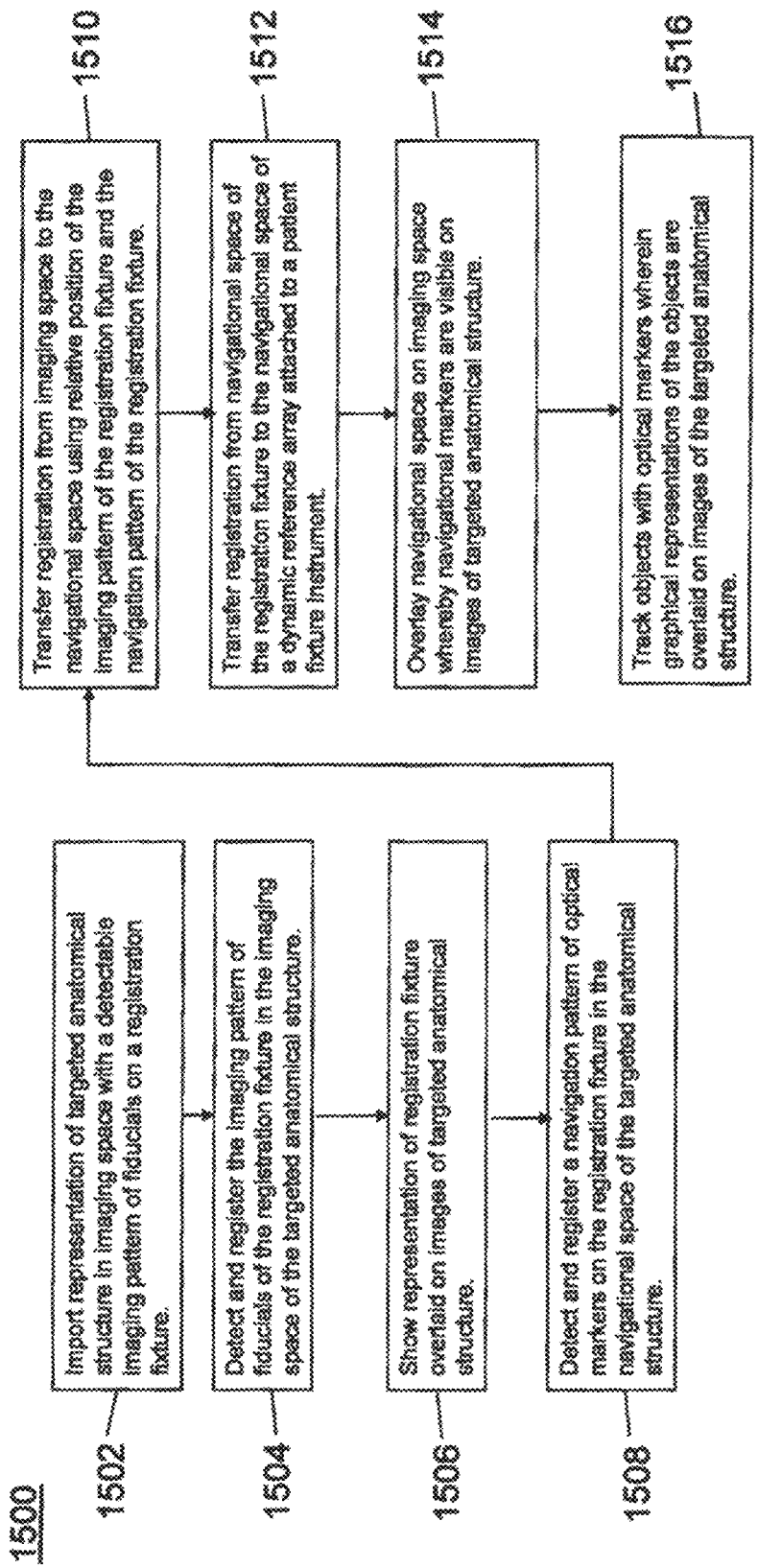
FIG. 11 illustrates a method of registration in accordance with an exemplary embodiment.

Referring to FIGS. 10 and 11, prior to or during a surgical procedure, certain registration procedures may be conducted in order to track objects and a target anatomical structure of the patient 210 both in a navigation space and an image space. In order to conduct such registration, a registration system 1400 may be used as illustrated in FIG. 10.

In order to track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 11 provides an exemplary method 1500 for registration consistent with the present disclosure. Method 1500 begins at step 1502 wherein a graphical representation (or image(s)) of the targeted anatomical structure may be imported into system 100, 300, 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

Figure 12A:
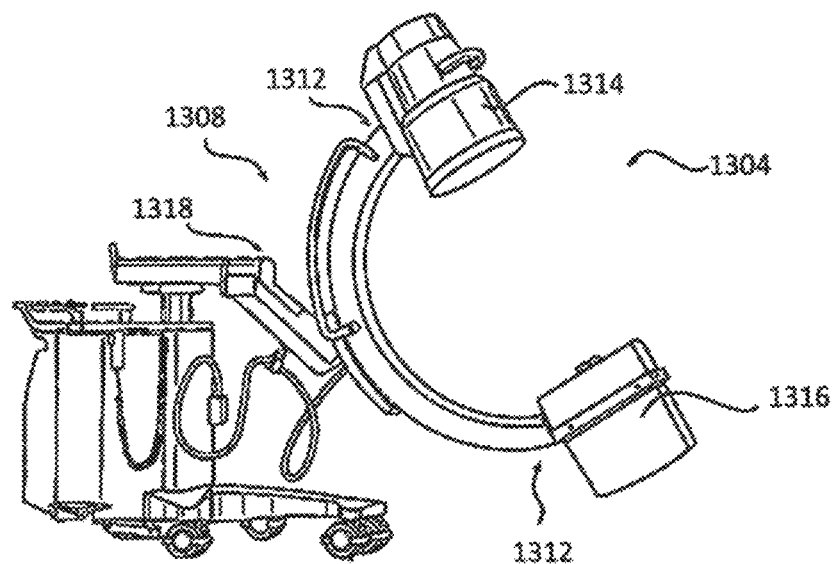
FIG. 12A-12B illustrate embodiments of imaging devices according to exemplary embodiments.
Figure 12B:
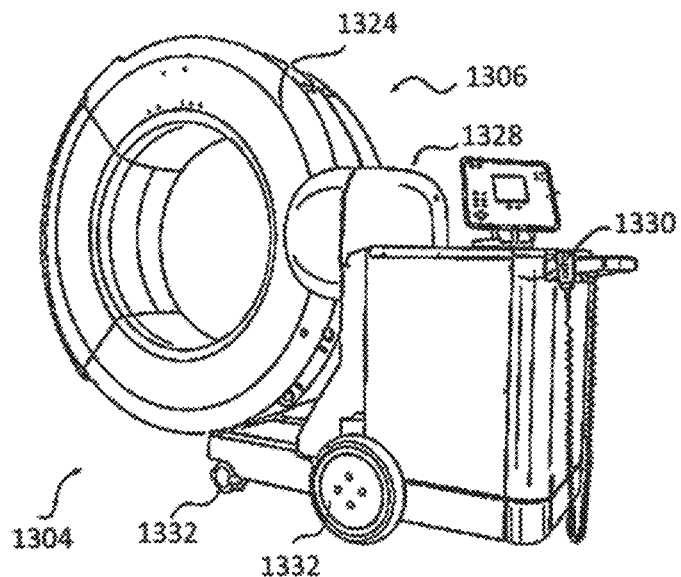

FIGS. 12A-12B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

FIGS. 13-17 illustrate exemplary images, systems, and/or methods for measuring the depth of surgical instrumentation during an operation on a patient. Implementations of the measurement systems and methods described may be conducted by the robot systems as previously described including robot systems 100, 300, and 600 and the components discussed thereto.

As an exemplary embodiment, a surgeon may position a long shaft such as a dilator tube within a secondary tracked tube, such as the robot's end effector guide tube or a free tracked external guide tube, to a known depth. These components have also been discussed as noted above. The depth may be the exact depth needed such that the dilator tube contacts the target bone of the patient. By referencing the secondary tracked tube, measuring the depth of the dilator tube may be conducted without tracking the dilator tube itself.

Figure 14:
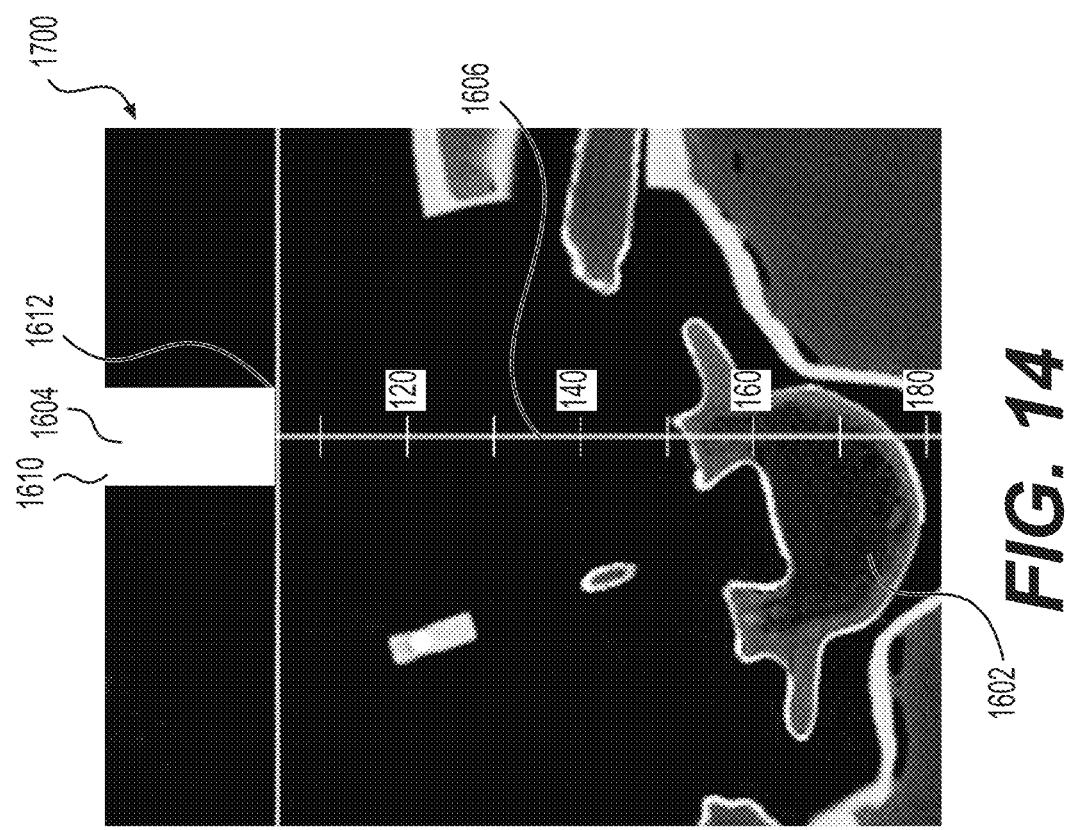
FIG. 14 illustrates an exemplary image of a viewplane of an x-ray with associated depictions measuring depth to a target bone.
Figure 13:
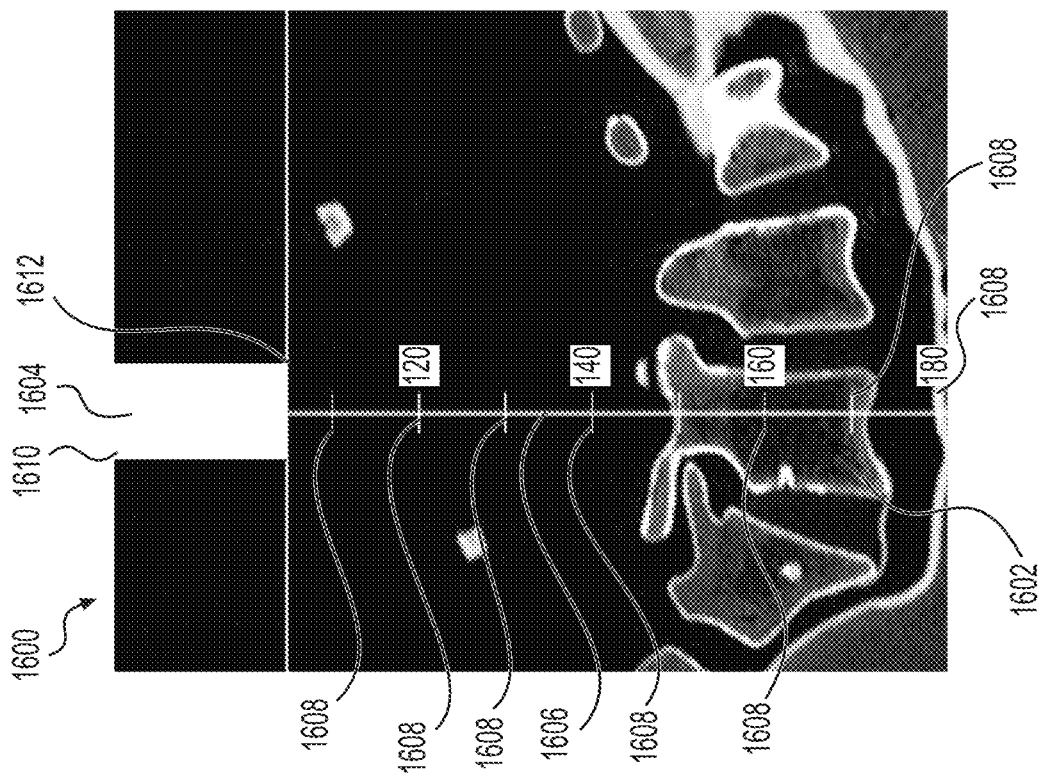
FIG. 13 illustrates an exemplary image of a viewplane x-ray with associated depictions measuring depth to a target bone.
Figures 15, 16, 17:
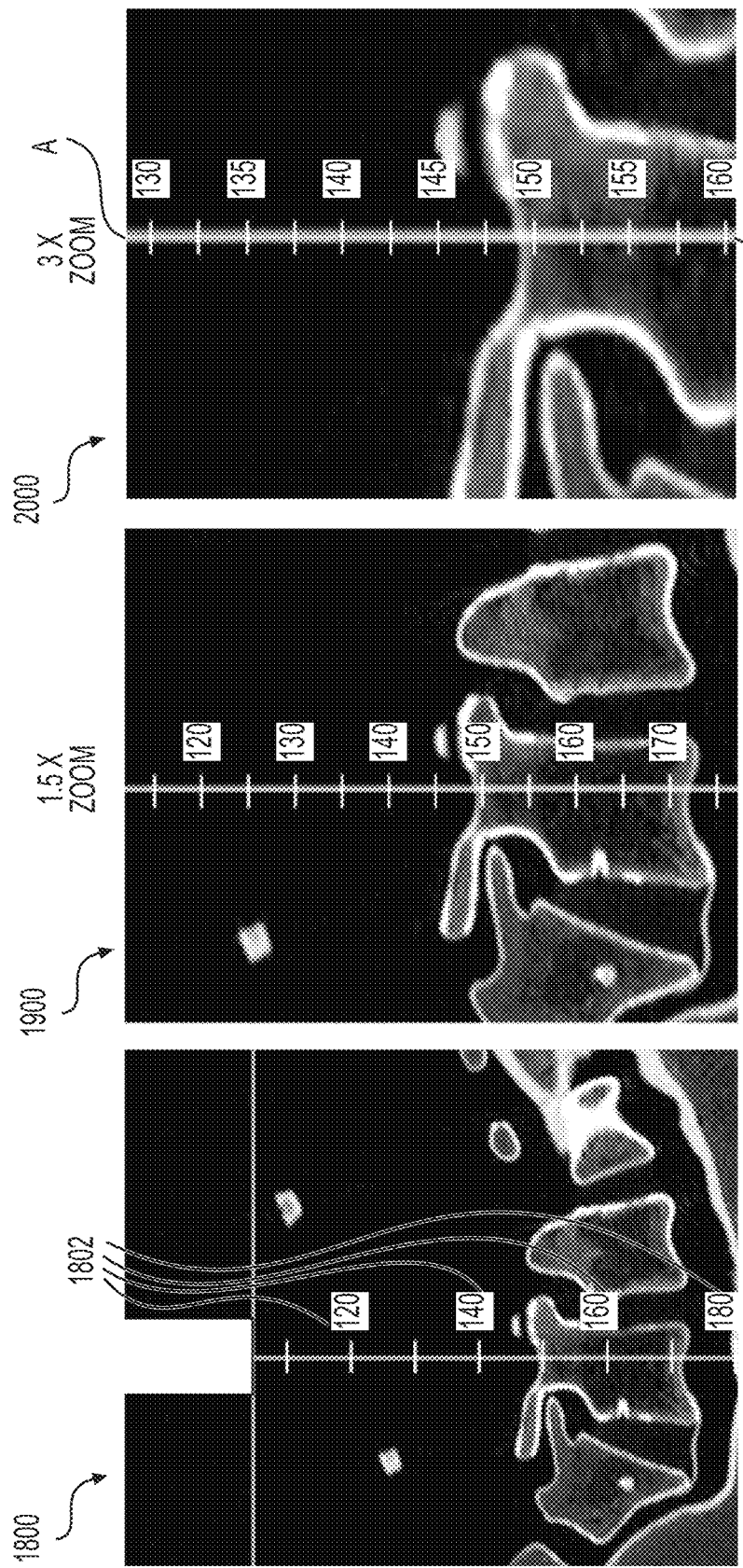
FIG. 15 illustrates an exemplary image of a viewplane of an x-ray with associated depictions measuring depth to a target bone.
FIG. 16 illustrates an exemplary image of a viewplane of an x-ray with associated depictions measuring depth to a target bone.
FIG. 17 illustrates an exemplary image of a viewplane of an x-ray with associated depictions measuring depth to a target bone.

Depth measurements may be based on the tracked guide tube—either the robot's end effector guide tube or other navigated guide tube—being in a "tube-centric" view. As an example, viewplanes of various CT scans of a patient's target bone may be chosen such that the 3D-tracked position of the guide tube (for example, positional tracking as earlier discussed) is aligned to be simultaneously within two non-parallel planes, or in other words coincident with the line formed by the intersection of two planes. For example, in a posterior surgery where the guide tube is aligned such that it is aimed down a pedicle of a vertebral body, two substantially orthogonal anatomical viewplanes may be selected such that one viewplane is predominantly sagittal, with the guide tube aligned along the vertical axis of the 2D viewplane, while the other viewplane is predominantly axial, with the guide tube also aligned along that 2D viewplane's vertical axis. FIG. 13 illustrates an exemplary 2D image plane (slice) 1600 through a 3D computed tomography (CT) image volume showing vertebrae of a patient, including vertebral body 1602, a guide tube 1604, and vector 1606 from a sagittal viewpoint of the patient. FIG. 14 illustrates an exemplary 2D image plane (slice) 1700 through a 3D CT image volume showing vertebral body 1602, guide 1604, and vector 1606 from an axial view point of the patient.

Although FIGS. 13 and 14 show particular viewplanes, other pairs of viewplanes could be selected such that the tracked guide tube's central axis is coincident with the line found from the intersection of the two planes. In addition, the 2D representation on each plane of the tube does not need to be vertical or even in the same direction in the two planes.

Vector 1606 may be depicted as extending from a representation of guide tube 1604 and overlaid on the images 1600 and 1700. On vector 1606, measurements may be shown incrementally with tick or hatch marks 1608. Marks 1608 may start from one end of guide tube 1604 (such as the top of proximal end 1610 and represented as position zero), with measurement increasing toward and beyond a distal end of the guide tube 1612. Guide tube 1604 may be coincident with the viewplanes because it is then known that any anatomical point along vector 1606 is reachable by a tool inserted through guide tube 1606. If guide tube 1604 was not coincident with the viewplanes, a vector may still be drawn but the vector may a projection on the 2D view that may not intersect the anatomy visualized on the viewplane.

Marks 1608 on vector 1606 may be toggled on or off as needed. Additionally, as a user independently zooms in or out on a viewplane, the frequency and labeling of marks 1608 may be automatically modified to minimize clutter while still providing useful information to the user regarding the depth. For example, as shown in images 1800, 1900, and 2000 of FIGS. 15, 16, and 17, respectively, labels 1802 could be included at a rate of one label every 20 mm and marks 1606 at a rate of one hatch mark every 10 mm for a particular level of zoom (See FIG. 15). As zoom is increased to 1.5 times the original zoom (compare FIG. 16 to FIG. 15), labels 1802 could automatically switch to a rate of one label every 10 mm and marks 1606 could automatically switch to a rate of one hatch mark every 5 mm. Then, as zoom is increased to 3.0 times the original zoom (compare FIG. 17 to FIGS. 15 and 16), labels 1802 could automatically switch to a rate of one label every 5 mm and the marks 1606 could automatically switch to a rate of one hatch mark every 2.5 mm.

As an example, the decision for automatically switching rate and frequency of marks 1606 and labels 1802 could be that between two points A and B, marks 1606 may be present from the first to the last visible point on a line crossing the viewplane along the guide tube's central vector. Within points A and B, an optimal selection would involve increments representing well rounded values, such as tens, fives, ones, halves, and quarters. The frequency of labeling may be a rate of one label every C marks. For example, these rules would be able to dictate the behavior shown in FIGS. 15-17 if A=10, B=15, C=2. With zooming, the surgeon could read with good precision the distance from the top of the guide tube to the bone, for example 149 mm in FIGS. 15-17.

Figure 18:
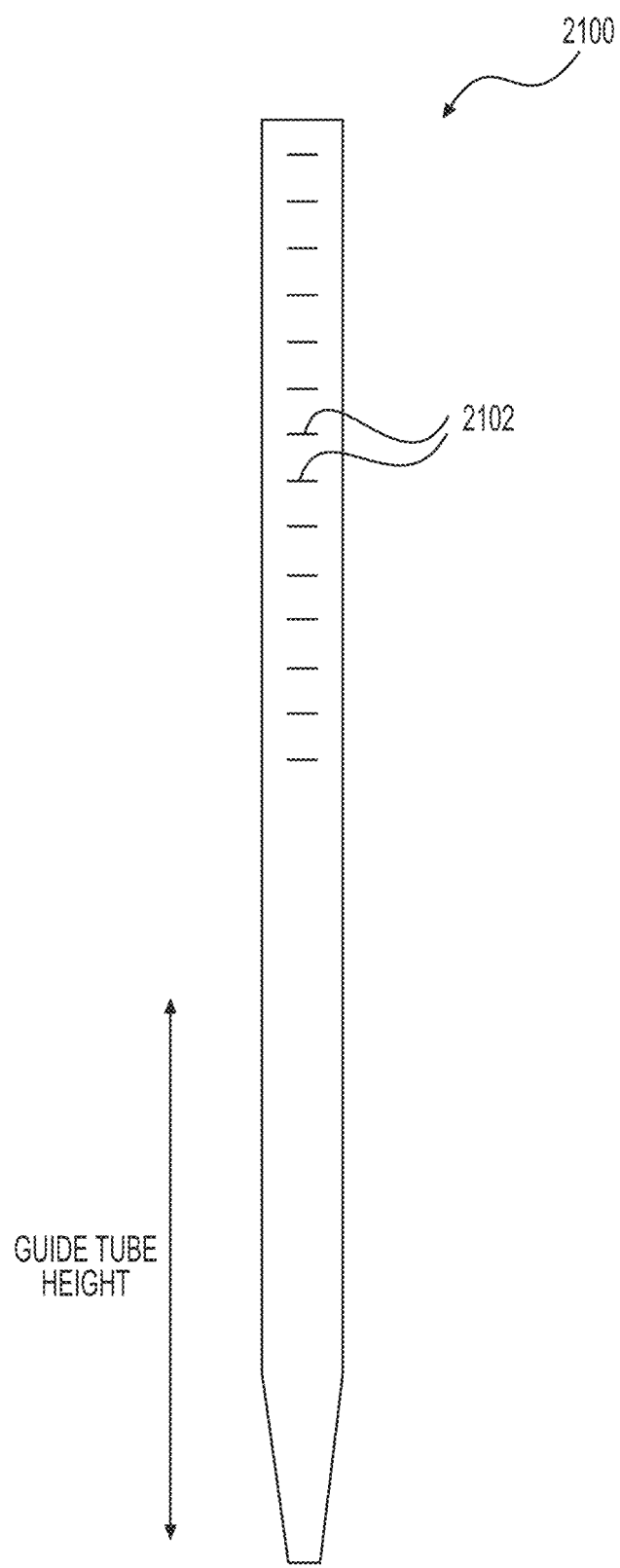
FIG. 18 illustrates an exemplary instrument with markings consistent with the present disclosure.

Using this measurement technique, the inserted instrument or dilator may have graduated markings and labels starting at zero at the distal end of the instrument and increasing toward the proximal end. FIG. 18 depicts an instrument 2100 with graduated markings 2102 showing this example. Markings 2102 may be present along the entire length of instrument 2100. In many cases, it may be unnecessary to include markings 2102 along the first length of instrument 2100 until the length of guide tube 1604 has been exceeded since markings 2102 would not be visible at the proximal end of guide tube 1604 with instrument 2100 inserted into guide tube 1604 and just beginning to protrude distally.

Figure 19:
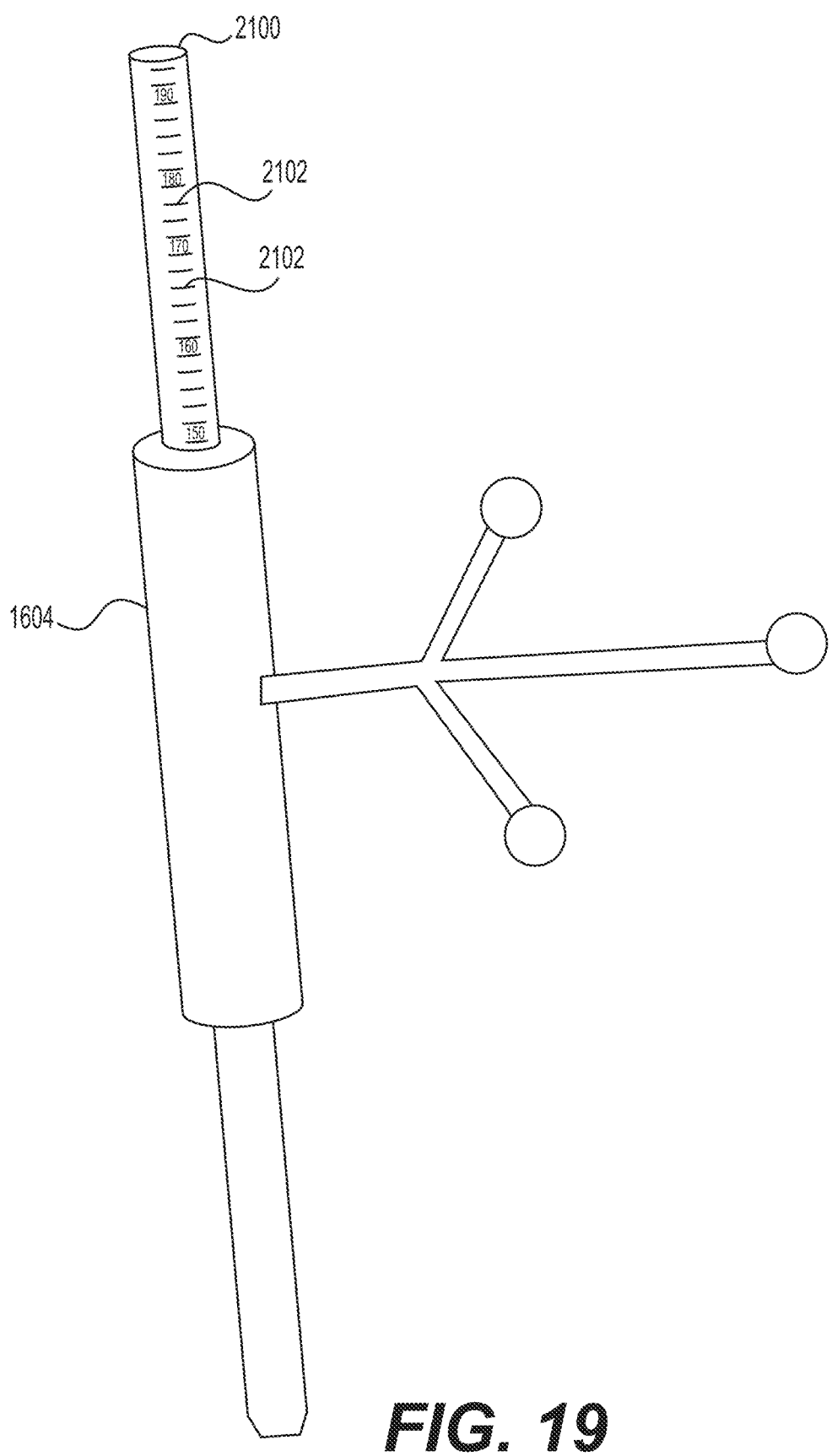
FIG. 19 illustrates an exemplary instrument and guide tube consistent with the present disclosure.

FIG. 19 illustrates instrument 2100, with markings 2102, inserted into guide tube 1604. The surgeon would insert instrument 2100 with markings into the tracked guide tube 1604 and would read the position of the inserted instrument 2100 from its graduations or markings 2102. This reading may indicate whether instrument 2100 reached the desired depth. For example, when inserting a dilator, if the length observed on markings 2102 agrees with a length measured from the measurement representing the distance from the proximal end of guide tube 1604 to the target bone of the patient, the surgeon would know that instrument 2100 was touching the target bone. If the length read from instrument 2100 was 3 mm less than the length from the measurement between the guide tube to the target bone, the surgeon would know that they must insert instrument 2100 a distance of 3 more millimeters before bone would be touched.

As described above, a distance from the top tip of instrument 2100 to the proximal end (top) of the tracked guide tube 1604 is being read from instrument 2100 by the use of markings 2102. Under the same principles of the present disclosure, measurement techniques may be configured such that the graphical images of the patient anatomy show the distance from the distal end (bottom) of tracked guide tube 1604, or the distance from a window through the guide tube 1604 to the tip of the instrument 2100. The insertion depth would then be read from these other locations, i.e., from the bottom of the guide tube or observed through a window in the guide tube, to draw the same information about the depth of insertion of the instrument.

Figure 20:
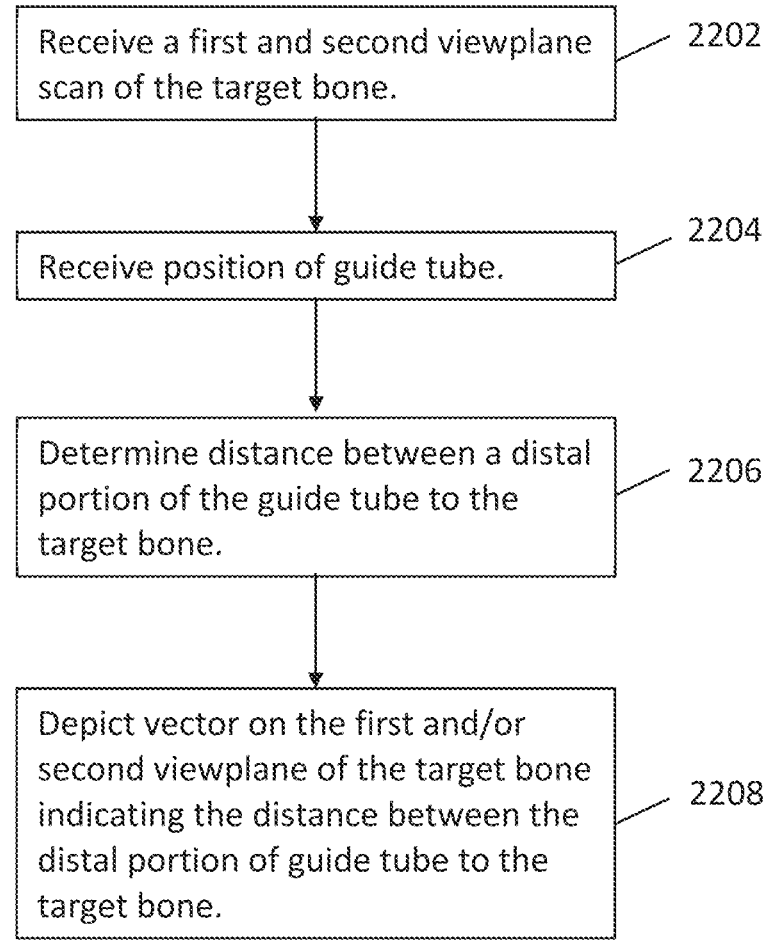
FIG. 20 illustrates an exemplary method consistent with the present disclosure.

FIG. 20 illustrates a method 2200 for determining the distance or depth in order to contact a target bone of patient consistent with the principles of the present disclosure. At step 2202 a computer subsystem, such as those previously described, receives a scan, for example a CT scan, that may represent the target bone of a patient from different viewplanes or viewpoints. The computer subsystem may receive a scan of a first viewplane and a second viewplane that form an intersection of views of the target bone in an image space. At step 2204, the computer subsystem may receive information indicative of a position of a guide tube of the surgical robot system in navigational space. At step 2206 the computer of the computer subsystem may determine a distance between a distal portion of the guide tube to the target bone of the patient. The distance may be determined such that a central axis of the guide tube is coincident to the line of intersection formed between the first viewplane and the second viewplane. At step 2608 the computer subsystem may display a vector indicative of the distance to contact the target bone of the patient on at least one of the first viewplane scan and the second viewplane scan. The vector may include any or all of the attributes a previously describe and those skilled in the art would recognize that the visual depiction of the vector may be represented in other way to indicate distance measurements that would fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A surgical system configured to indirectly determine a depth of a surgical tool relative to a target bone of a patient during a surgical operation based on a tracked tool guide to which the surgical tool is slidably coupled, the system comprising:
the tracked tool guide having a tracking marker;
the surgical tool having depth markings and configured to slidably couple to the tool guide, the depth markings allowing a user to determine the depth of the surgical tool relative to the tool guide to which the surgical tool is slidably coupled;
a tracking subsystem having a position sensor that recognizes the tracking marker in a navigational space;
a platform interface module configured to receive a signal from the tracking subsystem indicative of a position of the tool guide based on the recognized tracking marker;
a computer subsystem, including a computer and a display, configured to receive a first viewplane slice of the target bone from a 3D image volume of the patient;
wherein the computer is configured to receive the position of the tool guide from the platform interface module, and display in the display the received first viewplane slice and a vector overlaid on the first viewplane slice which is indicative of the depth to contact the target bone of the patient relative to the tool guide, thereby allowing the user to compare a desired depth based on the displayed vector and an actual depth of the surgical tool relative to the tracked tool guide.

2. The system of claim 1, wherein the computer displays in the display a virtual representation of the tool guide and the vector including a plurality of evenly spaced markings that indicate the depth from the tool guide towards the target bone.

3. The system of claim 1, wherein the computer is configured to reduce the increments of the markings as the user zooms in on the displayed first viewplane slice.

4. The system of claim 1, wherein the tool guide includes a tube which is part of an end effector of a robot and the surgical tool is configured to be inserted into the tube.

5. The system of claim 2, wherein the surgical tool contains graduated markings indicating the actual depth of the surgical tool past a selected point of the tool guide.

6. The system of claim 1, wherein:
the computer is configured to receive a second viewplane slice of the target bone from the 3D image volume of the patient, the second viewplane slice intersecting with the first viewplane slice at an angle in the 3D image volume;
wherein the computer is configured to display in the display the received second viewplane slice and a vector overlaid on the second viewplane slice which is indicative of the depth to contact the target bone of the patient relative to the tool guide.

7. The system of claim 1, wherein the surgical tool includes a dilator having the graduated markings and configured to be inserted into the tool guide.

8. A method for indirectly determining a depth of a surgical tool relative to a target bone of a patient during a surgical operation based on a tracked tool guide to which the surgical tool is slidably coupled, the method comprising:
receiving, by a computer subsystem having a computer and a display, a first viewplane slice of the target bone from a 3D image volume of the patient;
slidably coupling a surgical tool to the tracked tool guide having a tracking marker, the surgical tool having depth markings allowing a user to determine the depth of the surgical tool relative to the coupled tool guide;
receiving a signal from a position sensor indicative of a position of the tool guide based on the tracking marker;
determining, by the computer subsystem, a position of the tool guide in navigational space based on the received signal;
displaying in the display the first viewplane slice and a vector overlaid on the first viewplane slice which is indicative of the depth to contact the target bone of the patient relative to the tool guide, thereby allowing the user to compare a desired depth of the surgical tool based on the displayed vector and the actual depth of the surgical tool relative to the tool guide based on the depth markings.

9. The method of claim 8, wherein the step of displaying includes displaying a virtual representation of the tool guide and the vector including a plurality of evenly spaced markings that indicate the depth from the tool guide towards the target bone.

10. The method of claim 8, wherein the step of displaying includes changing the increments of markings in the vector automatically based upon a level of zoom.

11. The method of claim 8, wherein:
the tool guide includes a guide tube which is part of an end effector of a robot arm; and
the step of slidably coupling includes inserting the surgical tool into the guide tube.

12. The method of claim 11, wherein the surgical tool contains graduated markings indicating the actual depth of the surgical tool past a selected point of the guide tube.

13. The method of claim 8, wherein:
the step of receiving includes receiving a second viewplane slice of the target bone from the 3D image volume of the patient, the second viewplane slice intersecting with the first viewplane slice at an angle in the 3D image volume;
the step of displaying includes displaying the received second viewplane slice and a vector overlaid on the second viewplane slice which is indicative of the depth to contact the target bone of the patient relative to the tool guide.

14. The method of claim 8, wherein:
the tool guide includes a guide tube which is part of an end effector of a robot arm; and
the step of slidably coupling includes inserting a dilator with depth markings into the guide tube.

15. The method of claim 11, wherein the tool guide is attached to an end effector and the tool guide is tracked separately from the end effector.

* * * * *